(12) United States Patent
Robertson et al.

(10) Patent No.: US 7,745,147 B2
(45) Date of Patent: Jun. 29, 2010

(54) METHODS AND USES OF ANTIBODIES IN THE PURIFICATION OF INTERFERON

(75) Inventors: Colin Robertson, Midlothian (GB); Julie Smith, Midlothian (GB); Erik Lundgren, Umea (SE); Sven Lundberg, Umea (SE)

(73) Assignee: ViraNative AB, Umea (SE)

( * ) Notice: Subject to any disclaimer, the term of this patent is extended or adjusted under 35 U.S.C. 154(b) by 0 days.

(21) Appl. No.: 11/884,324

(22) PCT Filed: Feb. 13, 2006

(86) PCT No.: PCT/GB2006/000471

§ 371 (c)(1), (2), (4) Date: Sep. 2, 2008

(87) PCT Pub. No.: WO2006/085092

PCT Pub. Date: Aug. 17, 2006

(65) Prior Publication Data

US 2008/0319170 A1    Dec. 25, 2008

Related U.S. Application Data

(60) Provisional application No. 60/771,622, filed on Feb. 9, 2006.

(30) Foreign Application Priority Data

Feb. 12, 2005  (GB) ................... 0502991.3

(51) Int. Cl.
*G01N 33/53* (2006.01)
*A61K 38/21* (2006.01)
*C07K 1/14* (2006.01)
*C07K 1/18* (2006.01)
*C07K 14/56* (2006.01)

(52) U.S. Cl. .............. 435/7.1; 530/389.2; 530/413; 436/1; 424/184.1; 514/12

(58) Field of Classification Search ................ None
See application file for complete search history.

(56) References Cited

U.S. PATENT DOCUMENTS

| 4,423,147 A | 12/1983 | Secher et al. ............... 435/68 |
| 4,902,618 A | 2/1990 | Berg ....................... 435/172.2 |
| 5,391,713 A | 2/1995 | Borg ........................ 530/351 |

FOREIGN PATENT DOCUMENTS

| WO | WO 99/64440 | 12/1999 |
| WO | WO 00/39280 | 7/2000 |
| WO | WO 2006/085092 | 8/2006 |

OTHER PUBLICATIONS

Andersson, et al. "Application of Four Anti-Human Interferon-α Monclonal Antibodies for Immunoassay and Comparative Analysis of Natural Interferon-α Mixtures", *Journal of Interferon Research*, 11:53-60 (1991).

Tolo, et al. "Development of a Highly Purified Multicomponent Leukocyte IFN-α Product", *Journal of Interferon and Cytokine Research* 21:913-920 (2001).

Kandefer-Szerszen, et al. "Three Separate Epitopes on Human IFN—α Variants Defined by Monoclonal Antibodies and Their Role in the Binding to Receptors", *Archivum Immunologiac at Therapiae Experimentalis*, 1992, 40, 241-246.

Lundgren, et al. "Interferon-α: a gene family in therapeutic use", *Journal of Pharmaceutical & Biomedical Analysis*, vol. 7, No. 2, pp. 233-238, 1989.

*Primary Examiner*—Gary B Nickol
*Assistant Examiner*—Fozia M Hamud
(74) *Attorney, Agent, or Firm*—Drinker Biddle & Reath LLP

(57) ABSTRACT

The present invention provides improved methods and uses of an immunoglobulin in the purification of an interferon composition. The methods of the invention provide for the use of a monoclonal antibody in the purification of an interferon composition comprising a plurality of interferon alpha subtypes. The use of the monoclonal antibody provides for the production of an interferon composition with a consistent proportion of interferon subtypes, providing a resulting improvement in simplicity of production of the resulting interferon composition.

18 Claims, 8 Drawing Sheets

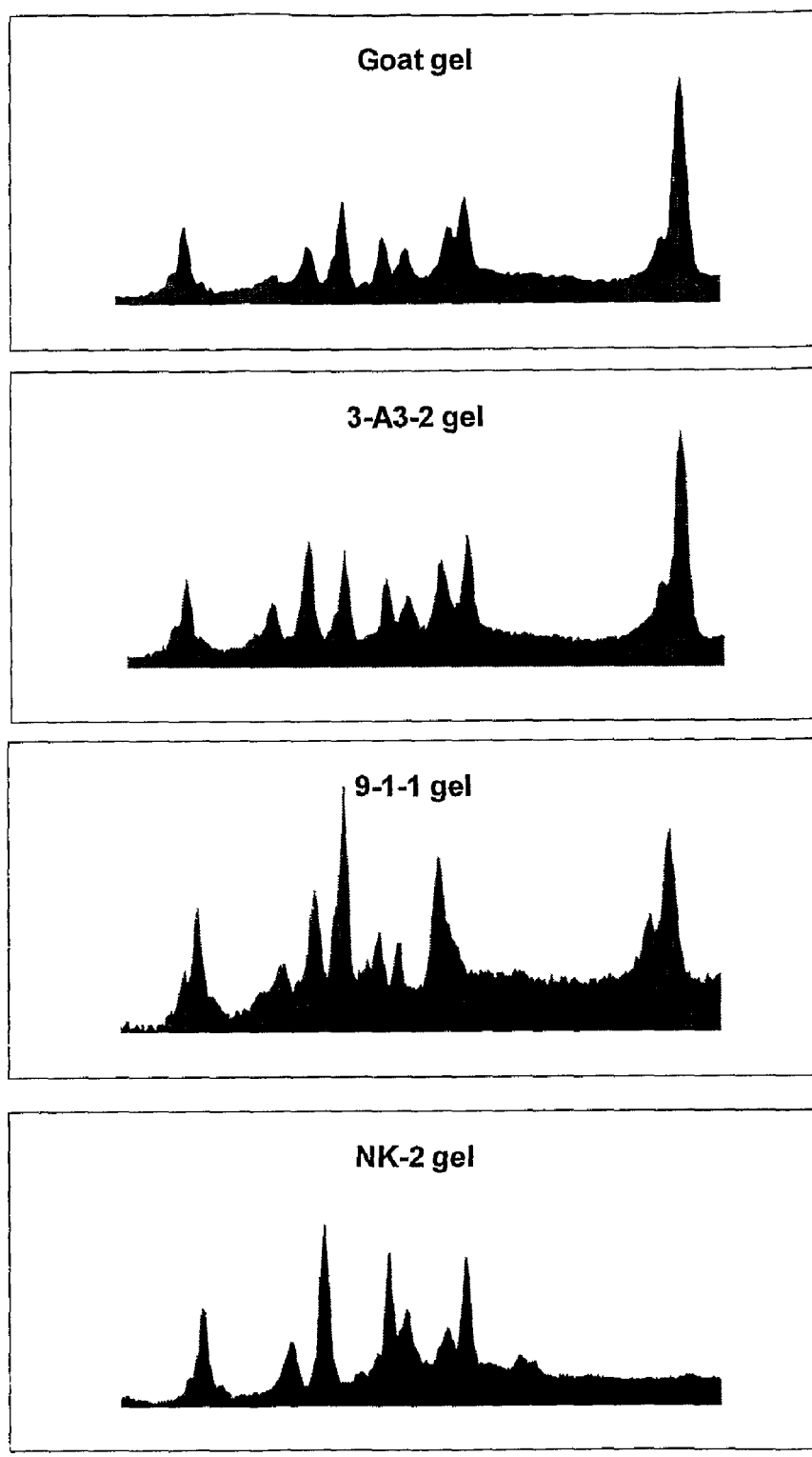
Figure 1 – Reversed-phase HPLC chromatograms for leukocyte interferon-alpha batch MS-112-089 purified on separate antibody immunoaffinity ligands (first batch)

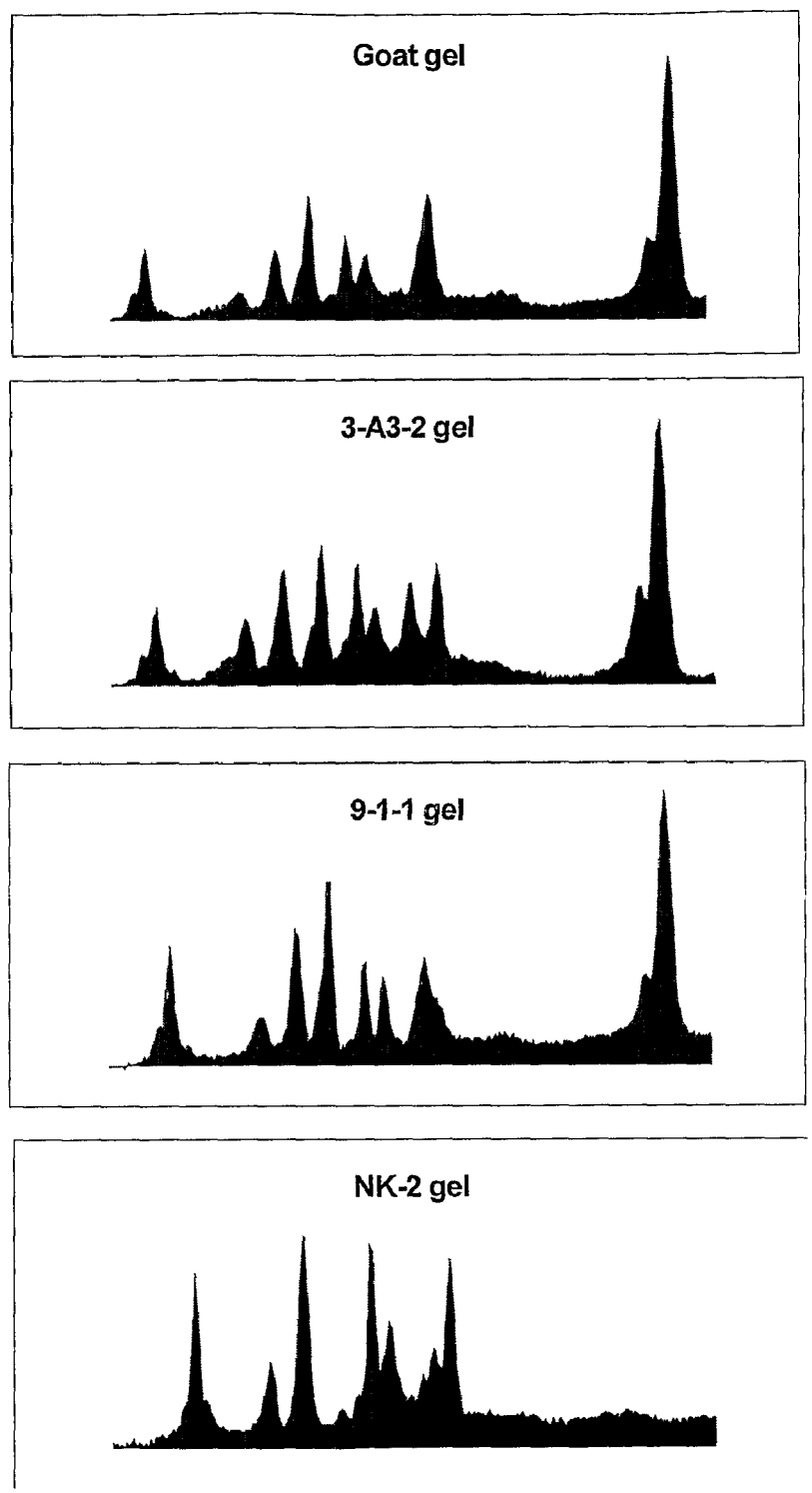
Figure 2. Reversed-phase HPLC chromatograms for leukocyte interferon-alpha batch MS-112-090 purified on separate antibody immunoaffinity ligands (second batch).

Figure 3. Typical MAb 3-A3-2 after affinity purification and formulation. The sample was run on SDS PAGE, with non-reduced (NR) and reduced (R) samples.
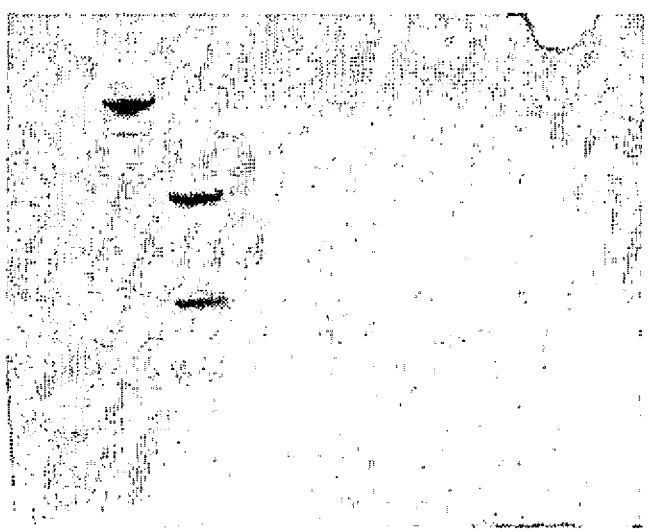

Figure 4. SDS-PAGE analysis of IFN-α88 recovered on MAb 3-A3-2 immunoaffinity column. Load, wash, and eluate fractions were silver stained after SDS-PAGE to show IFN-α88 protein recovered in the eluate.
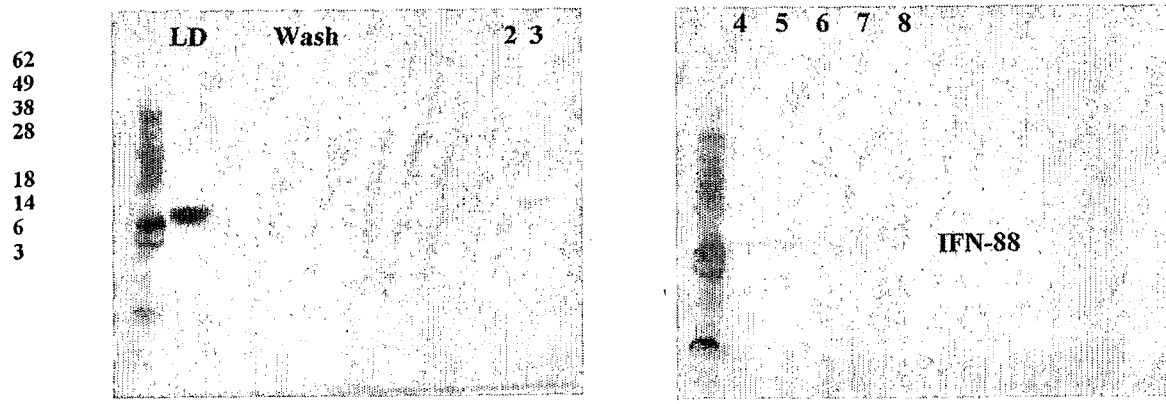

Figure 5. SDS-PAGE analysis of washes and eluate from LE50 interferon alpha variant purified on 3-A3-2 imm Figure 6. Subtype pattern for P-428 (purified using polyclonal Ab), and P-429 (purified using monoclonal Ab).
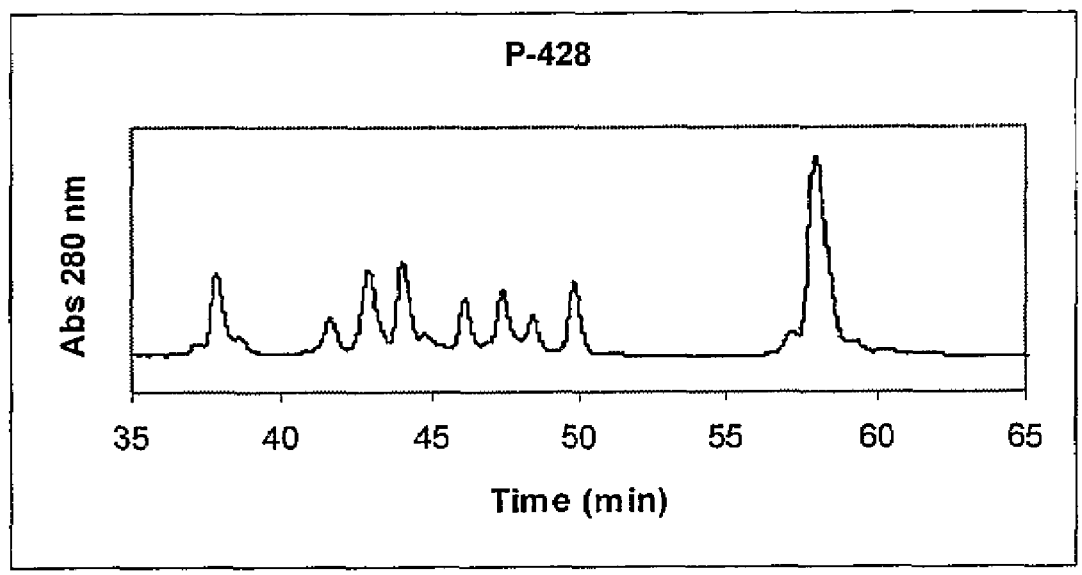
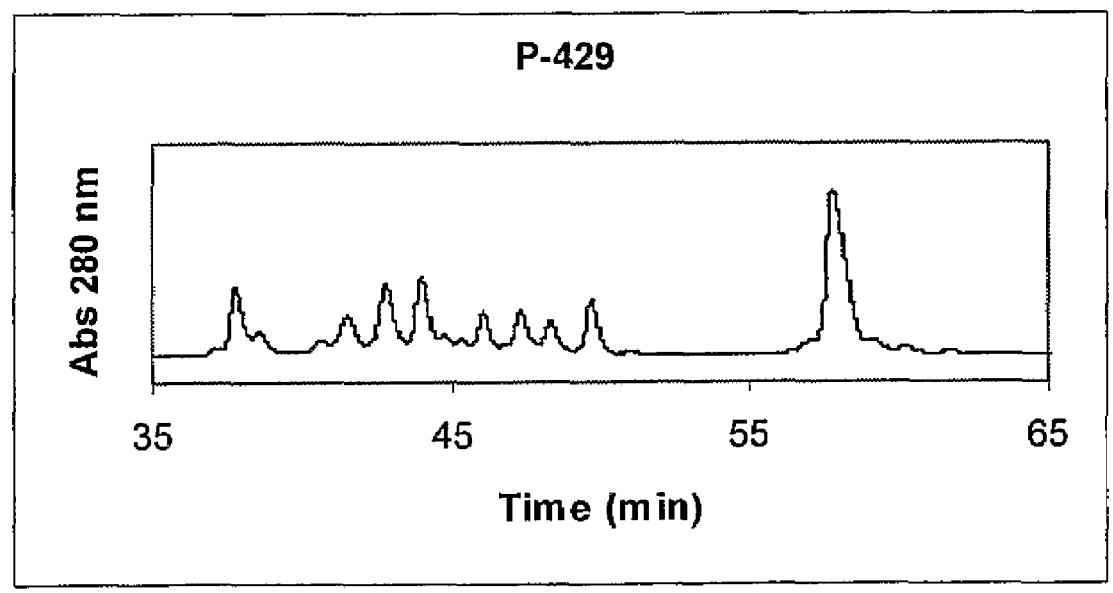

Figure 7 t gat ctg cct cag acc cac agc ctg ggt aat cgt cgt gcc ttg ata ctc ctg gca caa atg
   D  L  P  Q  T  H  S  L  G  N  R  R  A  L  I  L  L  A  Q  M(21)

gga aga att tct cct ttc tcc tgc ctg aag gac aga cat gac ttt gga ctt ccc cag gag gag
  G  R  I  S  P  F  S  C  L  K  D  R  H  D  F  G  L  P  Q  E  E(42)

ttt gat ggc aac cag ttc cag aag act caa gcc atc tct gtc ctc cat gag atg atc cag cag
  F  D  G  N  Q  F  Q  K  T  Q  A  I  S  V  L  H  E  M  I  Q  Q(63)

acc ttc aat ctc ttc agc aca gag gac tca tct gct gct tgg gaa cag agc ctc cta gaa aaa
  T  F  N  L  F  S  T  E  D  S  S  A  A  W  E  Q  S  L  L  E  K(84)

ttt tcc act gaa ctt tac cag caa ctg aat aac ctg gaa gca tgt gta ata cag gag gtt ggg
  F  S  T  E  L  Y  Q  Q  L  N  N  L  E  A  C  V  I  Q  E  V G(105)

atg gaa gag act ccc ctg atg aat gag gac tcc atc ctg gct gtg agg aaa tac ttc caa
  M  E  E  T  P  L  M  N  E  D  S  I  L  A  V  R  K  Y  F  Q(125)

aga atc act ctt tat cta aca gag aag aaa tac agc cct tgt gcc tgg gag gtt gtc aga gca
  R  I  T  L  Y  L  T  E  K  K  Y  S  P  C  A  W  E  V  V  R  A(146)

gaa atc atg aga tcc ctc tct ttt tca aca aac ttg caa aaa aga tta cgt cgt aag gat tga
  E  I  M  R  S  L  S  F  S  T  N  L  Q  K  R  L  R  R  K  D(166)

Figure 8a

CDLPQTHSLGNRRALILLAQMGRISPFSCLKDRHDFGLPQEE(42)

FDGNQFQKTQAISVLHEMIQQTFNLFSTEDSSAAWEQ R LLEK(84)

FSTELYQQLNNLEACVIQEVGMEETPLMNEDSILAVRKYFQ(125)

RITLYLTEKKYSPCAWEVVRAEIMRSLSFSTNLQKRLRRKD(166)

Figure 8b

CDLPQTHSLGNRRALILLAQMGRISPFSCLKDRHDFGLPQEE(42)

FDGNQFQKTQAISVLHEMIQQTFNLFSTEDSSAAWEQSLLEK(84)

FSTELYQQLNNLEACVIQEV W ME G TPLMNEDSILAVRKYFQ(125)

RITLYLTEKKYSPCAWEVVRAEIMRSLSFSTNLQKRLRRKD(166)

METHODS AND USES OF ANTIBODIES IN THE PURIFICATION OF INTERFERON

FIELD OF THE INVENTION

The present invention relates to improved methods and uses of antibodies for the purification of interferon products. More specifically, the present invention provides improved methods for the purification of a multiple subtype, naturally derived interferon alpha composition, wherein said composition has greater than 95 percent purity and is further characterised in that a particular proportion of interferon alpha (IFN-α) proteins are recovered.

BACKGROUND TO THE INVENTION

Human interferon alpha comprises a group of secretory proteins with anti-viral, anti-proliferative and immunoregulatory activities (Pestka et al., 1987). Type I interferons, comprising the interferon alpha (IFN-α) family have specific effects on gene transcription and translation. They are a part of innate immunity, and represent the first barrier against virus infection. Interferon alpha also blocks cell growth. Moreover, it regulates the immune system, both by regulation of HLA expression and direct activation of several classes of killer cells. The interferons therefore represent tremendous clinical potential.

The human interferon alpha proteins are encoded by a family of thirteen genes on human chromosome 9. Eleven interferon alpha proteins have been identified from culture medium supernatants of Sendai virus-induced human leukocytes (Nyman et al., 1998; Adolf et al., 1990; Pohl et al., 1994). The different gene products are designated as subtypes, some of which represent allelic variants (Golovleva et al., 1996). Two of the genes, IFNA1 and IFNA13 have identical coding sequences and produce a single protein species, but the other interferon alpha subtype proteins differ at the protein level by as much as 22 percent (Adolf et al., 1990).

The interferons have therapeutic activity against a wide variety of malignant and viral diseases, but in general, the therapeutic and clinical application of natural interferon alpha has been slow due to both the high cost of obtaining human interferon alpha and the difficulties in purifying the product. Recombinant interferons can be produced on a large scale by using genetic engineering. Such recombinant interferons, however, comprise just a single subtype (for example, Schering Plough's Intron A (IFN-α2b) or Roche's Roferon (IFN-α2a)). These recombinant, or synthetic forms lack any post-translational modification, and this may limit their biological activity. Furthermore, production of neutralising antibodies in patients receiving the recombinant forms may limit the effectiveness of the treatment (Lok et al., 1990; Jacobs et al., 1988; Weck et al., 1989). IFN-α derived from human leukocyte preparations does not, however, elicit such a response (von Wussow et al., 1987; Liao et al., 1992; Antonelli et al., 1991) and this reported difference represents a significant advantage for the use of the 'natural' forms of interferon alpha.

Patients who have neutralising antibodies, and therefore have to stop treatment with recombinant interferon alpha, can be treated successfully with natural (leukocyte) interferon alpha (von Wussow et al. 1991; Merup et al. 1994; Berg et al. 2001).

The general method for purification of interferon alpha from human leukocytes is typically derived from the 'Cantell' method described in 1981 by Kari Cantell and others, involving sequential protein precipitation. However, this process provides only a partial purification method in that the resulting preparation is only 1 percent pure for interferon alpha. Further processing is required to produce the purity of product necessary for large-scale production for clinical trials.

In manufacturing a multi-component product such as human leukocyte-derived interferon alpha for human clinical use, it is imperative that the number and proportion of interferon alpha subtype proteins produced should remain consistent through different batches. The manufacturers must have the required degree of control over the process to produce a consistently high quality product. One way in which this may be achieved is through the use of product-specific antibody ligands in the purification process.

European Patent Application No EP 0,478,659A (BioNative AB, Sweden) describes the use of a process to purify human leukocyte-derived interferon alpha, one of the steps comprising the use of polyclonal antibodies specific for interferon alpha obtained by immunisation of goats with a recombinant interferon alpha. The polyclonal antibodies are conjugated to an immunoaffinity column matrix, and consistently recognise the 6 major interferon alpha subtype proteins which can be detected and which are characteristic of the commercially available multi-subtype interferon product Multiferon™ (formerly called Interferon Alfanative™, Viragen Inc.).

U.S. Pat. No. 5,240,864 (Koga et al., JCR Pharmaceuticals Co., Ltd.) describes the use of polyclonal antibodies which recognise all interferon alpha subtype proteins, and the further separation of the polyclonal mixture to produce antibodies specific for each subtype.

Monoclonal antibodies have proven to be an invaluable tool for the characterisation, quantitation and purification of macromolecular antigens and have revolutionised the large-scale manufacture of many proteins, giving far greater purity, improved production efficiencies and, therefore, lower manufacturing costs.

The interferon alpha proteins represent an interesting case study. On one hand, the 80-90 percent amino acid homology includes interferon alpha subtype proteins that are sufficiently dissimilar to cause difficulties in producing monoclonal antibodies which would recognise all natural interferon alpha proteins in consistent proportions. However, at the same time, many subtype proteins show a sufficiently close degree of similarity, to create problems in obtaining interferon alpha protein-specific monoclonal antibodies (Berg, 1984; Alkan & Braun, 1986).

There are many reports of interferon alpha subtype-specific monoclonal antibodies being used in purification processes. U.S. Pat. No. 4,973,556 (Bove et al., Schering Corporation) describes the use of hybridomas and resulting monoclonal antibodies specific for the interferon alpha 2 subtype. The monoclonal antibodies produced by Secher and Burke (1980), and the corresponding U.S. Pat. No. 4,423,147, describe the preparation of a monoclonal antibody which is specific only to one subtype. Staehelin et al., 1981a and b, produced thirteen different hybridomas, each specific for a particular interferon alpha subtype. A number of the subtype-specific antibodies produced from the hybridomas were immobilised by conjugation to a solid support and shown to be able to recognise the corresponding interferon alpha subtype proteins in human leukocyte interferon alpha. Furthermore, the Finnish Red Cross utilise two monoclonal antibodies which recognise all nine interferon alpha subtype proteins in the manufacture of a multi-subtype human leukocyte interferon alpha (Tolo et al., 2001 and the corresponding International PCT Patent Application Publication No WO 99/64440).

It would be desirable to produce and utilise a monoclonal antibody having a broad spectrum of reactivity when developing a large-scale process for purification of human leukocyte interferon alpha proteins. To maintain a high degree of quality in a product destined for human use, it is necessary to demonstrate that a process is robustly consistent: in this case, this refers to the proportion of each interferon alpha protein measured in the final product. Furthermore, the use of one monoclonal antibody which recognises a broad range of interferon alpha subtype proteins would be economically advantageous: this is a crucial point to consider in large-scale production. It would therefore be desirable to utilise just one monoclonal antibody in the large-scale immunopurification of a multi-subtype interferon alpha destined for human use.

Most monoclonal antibodies recognise only a certain number of interferon alpha proteins. U.S. Pat. No. 5,503,828 (Testa et al. Interferon Sciences), describes a process for the large scale purification of interferon alpha using a monoclonal antibody known as NK-2, which recognises at least seven interferon alpha proteins, specifically subtypes α2, α4, α7, α8, α17 and α21, but not α1 which is the most abundant interferon alpha subtype protein in the naturally derived multi-subtype interferon alpha product Multiferon™. A monoclonal antibody with reactivity to a different set of interferon alpha proteins has also been reported (Tsukui et al., 1986). This monoclonal antibody, known as HT-1, recognised interferon proteins α1, α2, α4 and α6. Some monoclonal antibodies have been produced which can reportedly recognise many interferon alpha proteins. Berg (1984), and corresponding U.S. Pat. No. 4,902,618 (Berg, Wadley Technologies Inc.) describes the production and use of a hybridoma cell line which produces a monoclonal antibody which recognises twelve subtypes of interferon alpha.

Monoclonal Antibody 3-A3-2 and Multiferon™

The natural multi-subtype interferon alpha product Multiferon™ (Viragen Inc., Florida, USA) is manufactured from human leukocytes stimulated with Sendai virus. The culture is typically purified according to the process described in U.S. Pat. No. 5,391,713 (BioNative AB). This production method depends on the use of polyclonal antibodies for interferon alpha production. Multiferon™ is composed of at least 6 major interferon alpha proteins: predominantly α1, with lesser amounts of proteins α2, α8, α10, α14 and α21. Table 1 lists the prescribed proportions of each interferon alpha protein found in the final Multiferon™ product.

For proteins such as interferon alpha, which are on the whole expensive to manufacture, it would be desirable to be able to use a monoclonal antibody to provide an interferon composition with greater purity, stability and consistency that the equivalent composition derived from a production process which uses a polyclonal antibody mixture.

The present inventors have surprisingly identified that when the monoclonal antibody 3-A3-2 is used in a process for the isolation and purification of human interferon alpha subtypes, the resulting interferon composition is identical in terms of interferon alpha subtype composition and proportions, to the interferon alpha subtype mix present in the natural multi-subtype interferon alpha product commercially available under the name Multiferon™. This composition was hitherto produced using goat derived polyclonal antibodies as described in U.S. Pat. No. 5,391,713. This observation is highly unexpected, as it could not have been predicted based on prior knowledge of the binding specificity of monoclonal antibody 3-A3-2.

SUMMARY OF THE INVENTION

According to a first aspect of the present invention there is provided a process for the purification of a crude human leukocyte interferon, said process comprising the steps of;
(a) passing a solution of crude interferon through an immunoaffinity adsorption column, said column having monoclonal antibody 3-A3-2 or a binding fragment thereof bound to a solid support;
(b) eluting antibody bound interferon alpha from the column using a buffer solution;
(c) purifying the eluate by either precipitation or by ion exchange chromatography; and
(d) recovering the precipitated, or ion exchange-concentrated interferon alpha obtained in step c).

In one embodiment the monoclonal antibody is secreted by the hybridoma cell line 3-A3-2 which has been deposited under the provisions of the Budapest Treaty with the European Collection of Cell Cultures (ECACC), Porton Down, Salisbury, Wiltshire, SP4 0JG, United Kingdom, on Mar. 2, 2005, under accession number 05030201.

In a further embodiment the antibody or binding fragment thereof has a heavy chain variable region amino acid sequence of SEQ ID NO:1 or a sequence which is at least 80% homologous thereto.

In a still further embodiment the antibody or binding fragment thereof has a light chain variable region amino acid sequence of SEQ ID NO:2 or a sequence which is at least 80% homologous thereto.

In a yet further embodiment, the antibody or binding fragment thereof comprises a heavy chain amino acid sequence of SEQ ID NO:1 and a light chain variable amino acid sequence of SEQ ID NO:2 or sequences which are at least 80% homologous thereto.

Preferably the purified multi-subtype interferon alpha composition which is produced by the process of this aspect of the invention comprises interferon alpha proteins of subtypes alpha 1, alpha 2, alpha 8, alpha 10, alpha 14 and alpha 21. In a yet further embodiment, the interferon alpha 17 subtype may further be bound.

More preferably the purified multi-subtype interferon alpha composition which is produced by the method of this aspect of the invention comprises interferon alpha proteins at the following proportions by weight: interferon alpha 1 at 37+/−9%, alpha 2 plus alpha 21 at 30+/−7%, alpha 8 plus alpha 10 at 22+/−6%, and alpha 14 at 11+/−3%.

Most preferably, the interferon alpha composition comprises interferon alpha subtype proteins of proportions equivalent to those present in the commercially available multi-subtype natural interferon alpha product Multiferon™ (Viragen Inc).

In one embodiment, the process of this aspect of the invention is performed using a further step of concentrating the eluate from the immunoaffinity adsorption column using an ion exchange column. The interferon is suitably eluted from such ion exchange column by altering the pH. Such a pH increase can be obtained by applying a buffer solution to the column.

In addition to the precipitation step, using for example a thiocyanate solution, a further embodiment of the process may involve another precipitation step, wherein the interferon resulting from such precipitation is again precipitated in ethanol before its recovery.

After the single or double precipitation the interferon obtained is preferably subjected to gel filtration chromatography, and the proper eluent fractions having absorbance at 280 nm are collected and recovered.

In the precipitation step it is preferred to use a solution of potassium thiocyanate. Other precipitants suitable for use are trichloroacetic acid and ammonium sulphate. Elution of the interferon from the ion exchange column to concentrate the eluate from the preceding step is suitably performed by applying a buffer solution to alter the pH. Such pH alteration is preferably carried to a pH above neutral, such as to about 8.

Accordingly, in one embodiment, the process further comprises the step of purifying the eluate from the immunoaffinity adsorption column using an ion exchange column.

In a further embodiment, the precipitation of step (c) comprises a further secondary precipitation step, wherein the interferon resulting from this secondary precipitation step is further precipitated in ethanol prior to its recovery.

In a further embodiment, the precipitate is further subject to gel filtration, with effluent fractions having absorbance at 280 nm being collected and recovered.

In one embodiment the solid support comprises a matrix selected from the group consisting of an agarose bead, a polystyrene bead, a silica bead, a chelating agarose bead, and a magnetic bead.

In a further embodiment the antibody may be bound to carbohydrate, glass, silicon or another antibody. In a yet further embodiment the antibody may be bound to cyanogen bromide-activated (CNBr-activated) agarose. In a further still embodiment the antibody may be joined to the support through a linker. Advantageously, the linker serves to space the bound antibody molecules away from the surface of the microparticle, when in a bound state. The linker may be any suitable linker known to the person skilled in the art.

According to a second aspect of the present invention there is provided a multi-subtype interferon alpha composition prepared according to the process of the first aspect of the invention.

According to a third aspect of the present invention there is provided the use of a multi-subtype interferon alpha composition prepared according to the method of this aspect of the invention in the preparation of a medicament for the prevention or treatment of disease.

According to a fourth aspect of the present invention there is provided a method of purifying a multi-subtype interferon alpha composition, the method comprising the steps of:
- contacting crude interferon with monoclonal antibody 3-A3-2 or a binding fragment thereof bound to a solid support,
- eluting the adsorbed interferon from said support, and
- recovering a multi-subtype interferon alpha composition from the eluted interferon.

In one embodiment the monoclonal antibody is secreted by the hybridoma cell line 3-A3-2 which has been deposited according to ECACC accession number 05030201.

In a further embodiment the antibody or binding fragment thereof has a heavy chain variable region amino acid sequence of SEQ ID NO:1 or a sequence which is at least 80% homologous thereto.

In a still further embodiment the antibody or binding fragment thereof has a light chain variable region amino acid sequence of SEQ ID NO:2 or a sequence which is at least 80% homologous thereto.

In a yet further embodiment, the antibody or binding fragment thereof comprises a heavy chain amino acid sequence of SEQ ID NO:1 and a light chain variable amino acid sequence of SEQ ID NO:2 or sequences which are at least 80% homologous thereto.

In a yet further embodiment, the antibody or binding fragment thereof specifically binds to an epitope which is bound by the antibody produced by the hybridoma cell line deposited with the ECACC under accession number 05030201.

In one embodiment the solid support comprises a matrix selected from the group consisting of an agarose bead, a polystyrene bead, a silica bead, a chelating agarose bead, and a magnetic bead.

In a further embodiment the antibody may be bound to carbohydrate, glass, silicon or another antibody. In a yet further embodiment the antibody may be bound to cyanogen bromide-activated (CNBr-activated) agarose. In a further still embodiment the antibody may be joined to the support through a linker.

Preferably the purified multi-subtype interferon alpha composition which is produced by the method of this aspect of the invention comprises interferon alpha proteins of subtypes alpha 1, alpha 2, alpha 8, alpha 10, alpha 14 and alpha 21. In a yet further embodiment, preferably interferon alpha 17 subtype is further bound.

More preferably the purified multi-subtype interferon alpha composition which is produced by the method of this aspect of the invention comprises interferon alpha proteins at the following proportions by weight: interferon alpha 1 at 37+/−9%, alpha 2 plus alpha 21 at 30+/−7%, alpha 8 plus alpha 10 at 22+/−6%, and alpha 14 at 11+/−3%.

According to a further aspect of the present invention there is provided a multi-subtype interferon alpha composition prepared according to the method of the fourth aspect of the invention.

A yet further aspect of the invention provides for the use of a monoclonal antibody or a binding fragment thereof which specifically binds to at least one interferon alpha subtype in the preparation of an interferon alpha composition, wherein the monoclonal antibody is 3-A3-2 as secreted by the hybridoma 3-A3-2 which has been deposited according to ECACC accession number 05030201.

In one embodiment the interferon alpha composition is a multi-subtype interferon alpha composition.

In one embodiment the interferon alpha composition comprises interferon alpha subtypes alpha 1, alpha 2, alpha 8, alpha 10, alpha 14 and alpha 21. In a yet further embodiment, preferably interferon alpha 17 subtype is further bound.

In a yet further embodiment the interferon alpha composition comprises interferon alpha subtype proteins at the following proportions by weight: alpha 1 at 37+/−9%, alpha 2 plus alpha 21 at 30+/−7%, alpha 8 plus alpha 10 at 22+/−6%, and alpha 14 at 11+/−3%.

A yet further aspect of the present invention provides for the use of the multi-subtype interferon alpha composition prepared according to the method of this aspect of the invention in the preparation of a medicament for the prevention or treatment of disease.

A yet further aspect of the present invention provides for the use of a multi-subtype interferon alpha preparation prepared according to the invention in the preparation of a medicament for human healthcare applications, such as viral conditions and immunological disorders including cancer, malignant conditions including malignant melanoma, hairy cell leukaemia and chronic myelogenous leukaemia, multiple sclerosis, human immunodeficiency virus (HIV), acquired immune deficiency syndrome (AIDS), hepatitis B, hepatitis C, herpes, avian influenza and other subtypes of type A influenza virus of the family orthomyxoviridae, coronavirus infection and severe acute respiratory syndrome (SARS).

A yet further aspect of the present invention provides for an immunopurification process for the isolation of specific interferon alpha subtype proteins from a sample containing at least one interferon alpha protein, comprising the steps of;
passing the sample through an immunoabsorbent column having 3-A3-2 monoclonal antibody or a binding fragment thereof bound to a solid support,
eluting adsorbed interferon from said support, and
recovering at least one interferon alpha subtype protein from the eluted interferon.

In one embodiment the solid support comprises a matrix selected from the group consisting of an agarose bead, a polystyrene bead, a silica bead, a chelating agarose bead, and a magnetic bead.

In a further embodiment the antibody may be bound to carbohydrate, glass, silicon or another antibody. In a yet further embodiment the antibody may be bound to cyanogen bromide-activated (CNBr-activated) agarose. In a further still embodiment the antibody may be joined to the support through a linker.

A further aspect of the present invention provides for the use of the monoclonal antibody 3-A3-2 or a binding fragment thereof as an immunoaffinity ligand in method for the production of an interferon composition comprising a defined proportion of interferon alpha subtype proteins from culture medium.

The invention also extends to a purified human leukocyte interferon whenever prepared by the methods and processes described herein.

A yet further aspect of the present invention provides a monoclonal antibody or binding fragment thereof which specifically binds to interferon alpha subtypes alpha 1, alpha 2, alpha 8, alpha 10, alpha 14 and alpha 21, having a heavy chain variable sequence as defined in SEQ ID NO:1 or a sequence which is at least 80% homologous thereto and/or a light chain variable sequence as defined in SEQ ID NO:2 or a sequence which is at least 80% homologous thereto.

A further still aspect of the present invention provides a monoclonal antibody or binding fragment thereof which specifically binds to interferon alpha subtypes alpha 1, alpha 2, alpha 8, alpha 10, alpha 14 and alpha 21, said monoclonal antibody being 3-A3-2 and being secreted by the hybridoma which has been deposited under the provisions of the Budapest Treaty with the European Collection of Cell Cultures (ECACC), Porton Down, Salisbury, Wiltshire, SP4 0JG, United Kingdom, on Mar. 2, 2005, under accession number 05030201.

A yet further aspect of the present invention provides for the use of a monoclonal antibody designated 3-A3-2 as deposited under the provisions of the Budapest Treaty with the European Collection of Cell Cultures (ECACC), Porton Down, Salisbury, Wiltshire, SP4 0JG, United Kingdom, on Mar. 2, 2005, under accession number 05030201, or a binding fragment thereof in an assay or in the purification or isolation of an interferon alpha protein of the subtype alpha 1, alpha 2, alpha 8, alpha 10, alpha 14, alpha 17 or alpha 21.

Antibodies

An "antibody" is an immunoglobulin, whether natural or partly or wholly synthetically produced. The term also covers any polypeptide, protein or peptide having a binding domain that is, or is homologous to, an antibody binding domain. These can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb, Fd, and a bi-specific antibody.

As antibodies can be modified in a number of ways, the term "antibody" should be construed as covering any binding member or substance having a binding domain with the required specificity. The antibody of the invention may be a monoclonal antibody, or a fragment, derivative, functional equivalent or homologue thereof. The term includes any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in European Patent Application Publication Number EP 0,120,694 and European Patent Application Publication Number EP 0,125,023.

The constant region of the antibody may be of any suitable immunoglobulin subtype, however it is preferred that the antibody subtype is IgG1. However, in alternative embodiments, the subtype of the antibody may be of the class IgA, IgM, IgD and IgE where a human immunoglobulin molecule is used. Such an antibody may further belong to any sub class e.g. IgG1, IgG2a, 2b, IgG3 and IgG4. In further embodiments, the constant region may be derived from an immunoglobulin subtype from a non-human source such as any other animal, in particular a mouse.

Fragments of a whole antibody can perform the function of antigen binding. Examples of such binding fragments are; a Fab fragment comprising of the VL, VH, CL and CH1 antibody domains; an Fv fragment consisting of the VL and VH domains of a single antibody; a F(ab')2 fragments, a bivalent fragment comprising two linked Fab fragments; a single chain Fv molecule (scFv), wherein a VH domain and a VL domain are linked by a peptide linker which allows the two domains to associate to form an antigen binding site; or a bi-specific antibody, which may be multivalent or multispecific fragments constructed by gene fusion.

A fragment of an antibody or of a polypeptide for use in the present invention, for example, a fragment of the 3-A3-2 antibody, generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids. A preferred group of fragments are those which include all or part of the CDR regions of monoclonal antibody 3-A3-2.

A "derivative" of such an antibody or polypeptide, or of a fragment of a 3-A3-2 antibody means an antibody or polypeptide modified by varying the amino acid sequence of the protein, e.g. by manipulation of the nucleic acid encoding the protein or by altering the protein itself. Such derivatives of the natural amino acid sequence may involve insertion, addition, deletion and/or substitution of one or more amino acids, preferably while providing a peptide having interferon alpha binding activity. Preferably such derivatives involve the insertion, addition, deletion and/or substitution of 25 or fewer amino acids, more preferably of 15 or fewer, even more preferably of 10 or fewer, more preferably still of 4 or fewer and most preferably of 1 or 2 amino acids only.

The term "antibody" includes antibodies which have been "humanised". Methods for making humanised antibodies are known in the art. Methods are described, for example, in Winter, U.S. Pat. No. 5,225,539. A humanised antibody may be a modified antibody having the hypervariable region of a monoclonal antibody such as 3-A3-2 and the constant region of a human antibody. Thus the binding member may comprise a human constant region.

The variable region other than the hypervariable region may also be derived from the variable region of a human antibody and/or may also be derived from a monoclonal antibody such as 3-A3-2. In such case, the entire variable region may be derived from murine monoclonal antibody 3-A3-2 and the antibody is said to be chimerised. Methods for making chimerised antibodies are known in the art. Such methods include, for example, those described in U.S. patents by Boss (Celltech) and by Cabilly (Genentech). See U.S. Pat. Nos. 4,816,397 and 4,816,567, respectively.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184,187, GB 2,188,638A or EP-A-239,400. A hybridoma or other cell producing an antibody may be subject to genetic mutation or other changes, which may or may not alter the binding specificity of antibodies produced.

As used herein, reference to "3-A3-2" includes sequences which show substantial homology with 3-A3-2. Preferably the degree of homology between 3-A3-2 complementarity determining regions (CDRs) and the CDRs of other antibodies will be at least 60%, more preferably 70%, further preferably 80%, even more preferably 90% or most preferably 95%.

According to one embodiment, the 3-A3-2 antibody specifically binds to an epitope which is bound by the monoclonal antibody produced by the hybridoma cell line deposited with the ECACC under accession number 05030201.

The variable domain amino acid sequences for the heavy and light chains of the 3-A3-2 antibody product of the deposited 3-A3-2 hybridoma are as follows:

Variable Gamma Sequence. This is equivalent to the amino acid sequence of the variable domain of the heavy chain and is referred to herein as SEQ ID NO:1:

QVQLQESGTVLARPGASVKMSCKASGYSFTTYWMHWVKQRPGQGLEWIGV

IYPGNGDTTYNQKFKDKAKLTAVTSANTAYMELSSLTNEDSAVYFCTRNY

KYDYYTMDYWGQGTTVTVSS

Variable Kappa Sequence. This is equivalent to the amino acid sequence of the variable domain of the light chain and is referred to herein as SEQ ID NO:2:

DTVLTQSPASLAVSLGQRATISCRASKSVSTSGHSYMHWYQQKPGQTPKL

LIYLASNLESGVPARFSGSGSGTDFTLNIHPVEEEDAATYYCQHSGELPF

TFGSGTKLEIK

The percent identity of two amino acid sequences or of two nucleic acid sequences may be determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those skilled in the art. An example of a mathematical algorithm for comparing two sequences is the algorithm of Karlin and Altschul (1990), modified as in Karlin and Altschul (1993). The NBLAST and XBLAST programs of Altschul, et al. (1990) have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilised as described in Altschul et al. (1997). Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.nlm.nih.gov.

Where high degrees of sequence identity are present there will be relatively few differences in amino acid sequence. Thus for example there may be less than 20, less than 10, or even less than 5 differences.

Production of Antibodies

The antibodies or antibody fragments of and for use in the present invention may be generated wholly or partly by chemical synthesis. The antibodies can be readily prepared according to well-established, standard liquid or, preferably, solid-phase peptide synthesis methods, general descriptions of which are broadly available and are well known by the person skilled in the art. Further, they may be prepared in solution, by the liquid phase method or by any combination of solid-phase, liquid phase and solution chemistry.

Another convenient way of producing antibodies or antibody fragments suitable for use in the present invention is to express nucleic acid encoding them, by use of nucleic acid in an expression system. Thus the present invention further provides the use of an isolated nucleic acid encoding antibodies or antibody fragments which bind to interferon alpha proteins.

Nucleic acid for use in accordance with the present invention may comprise DNA or RNA and may be wholly or partially synthetic. In a preferred aspect, nucleic acid for use in the invention codes for antibodies or antibody fragments of the invention as defined above. The skilled person will be able to determine substitutions, deletions and/or additions to such nucleic acids which will still provide an antibody or antibody fragment of the present invention.

Nucleic acid sequences encoding antibodies or antibody fragments for use with the present invention can be readily prepared by the skilled person using the information and references contained herein and techniques known in the art (for example, see Sambrook et al. (1989), and Ausubel et al, (1992)), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding antibody fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The nucleic acid may be comprised as constructs in the form of a plasmid, vector, transcription or expression cassette which comprises at least one nucleic acid as described above. The construct may be comprised within a recombinant host cell which comprises one or more constructs as above. Expression may conveniently be achieved by culturing under appropriate conditions recombinant host cells containing the nucleic acid. Following production by expression the antibody or antibody fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells, NS0 mouse myeloma cells. A common, preferred bacterial host is E. coli.

The expression of antibodies and antibody fragments in prokaryotic cells such as E. coli is well established in the art. For a review, see for example Pluckthun (1991). Expression in eukaryotic cells in culture is also available to those skilled in the art as an option for production of a binding member, see for recent review, for example Reff, (1993); Trill et al., (1995).

Alternatively, antibodies or antibody fragments for use in the invention may be produced in transgenic organisms, for example mammals, avians, fish, insects or plants using methods known in the art.

In such transgenic methods, nucleic acid encoding the binding member(s) may be introduced to the cell or embryo by methods including but not limited to direct injection, electroporation, nuclear transfer techniques or by use of vectors, e.g. viral vectors such as lentiviral vectors. In one preferred embodiment, the specific binding members are produced in avian tissues, preferably avian eggs, using, for example, the method as disclosed in PCT Patent Application Publication No WO 04/047531.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Sambrook et al., (1989). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. eds., (1992).

The nucleic acid may be introduced into a host cell by any suitable means. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells under conditions for expression of the gene.

The nucleic acid may be integrated into the genome (e.g. chromosome) of the host cell. Integration may be promoted by inclusion of sequences which promote recombination with the genome in accordance with standard techniques. The nucleic acid may be on an extra-chromosomal vector within the cell, or otherwise identifiably heterologous or foreign to the cell.

Preferred features of each aspect and embodiment of the invention are as for each of the other aspects mutatis mutandis unless the context demands otherwise.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

DETAILED DESCRIPTION OF THE INVENTION

The invention will now be exemplified herein with reference to the following non-limiting examples which are provided for the purpose of illustration and are not to be construed as being limiting on the present invention. Further, reference is made to the accompanying figures wherein;

FIG. 1 shows reversed-phase HPLC chromatograms for leukocyte interferon-alpha batch MS-112-089 purified on separate antibody immunoaffinity ligands, FIG. 2 shows reversed-phase HPLC chromatograms for leukocyte interferon-alpha batch MS-112-090 purified on separate antibody immunoaffinity ligands, FIG. 3 shows typical Monoclonal antibody 3-A3-2 TFF concentrate sample run on SDS-PAGE, with non-reduced (NR) and reduced (R) samples, FIG. 4 shows silver stained protein bands following elution of interferon alpha 88 from a Monoclonal antibody 3-A3-2 immunoaffinity column, FIG. 5 shows SDS-PAGE gel of interferon alpha variant LE50 processed through 3-A3-2 immunoaffinity chromatography, FIG. 6 shows reversed-phase HPLC chromatograms for leukocyte interferon-alpha recovered using goat polyclonal antibody and Monoclonal antibody 3-A3-2 immunoaffinity columns, FIG. 7 shows the full DNA sequence (SEQ ID NO: 17) and predicted primary amino acid sequence (SEQ ID NO: 18) of the cloned PCR product from the bacterially-derived recombinant plasmid pIFNα88NC-P6, and FIGS. 8a and 8b show the predicted amino acid sequence of pLE60 (SEQ ID NO: 19) and pLE61 (SEQ ID NO: 20), altered amino acids are shown in bold text.

Monoclonal antibody 3-A3-2 was derived from a three month old female BALB/c mouse immunised with a recombinant interferon alpha protein known as interferon alpha 88 (Lund et al., 1985). The fusion partner is SP2/0 myeloma cells (Andersson et al., 1991) and the isotype is IgG1/κ. Andersson and colleagues compared the 3-A3-2 monoclonal antibody with three other monoclonal antibodies for their abilities to bind to interferon alpha proteins (namely the "19K" protein, which is α1, and subtypes α2a, α2b, α2c and α88) in different assays. It was found that in solution, the 3-A3-2 monoclonal antibody only bound to interferon alpha 88, whereas when the interferon alpha protein was bound to a solid support, the monoclonal recognised interferon alpha 88 strongest, followed by the interferon alpha 2a and interferon alpha 2b subtypes. Neither the interferon alpha 2c nor the interferon alpha 1 proteins were recognised. Furthermore, in optimal ELISAs, monoclonal 3-A3-2 could recognise all interferon alpha proteins except interferon alpha 1 (interferon alpha 88 was recognised best). These data contrast with the inventors, findings that demonstrate that monoclonal 3-A3-2 coupled to Sepharose beads is able to recover interferon alpha 1 (and other interferon alpha subtype proteins) from solution. This work is described in Examples 1, 3, 4 and 5.

The data thus show that the ability of monoclonal 3-A3-2 and other monoclonals to recognise interferon alpha subtype proteins depends largely on how the interferon alpha itself is presented to the monoclonal. It was recognised in another study comparing monoclonal antibody abilities to bind interferon alpha that "interferons are flexible molecules" (Alkan and Braun, 1986). It is therefore expected that the site on the interferon alpha molecule to which the antibody binds, is largely conformationally-defined.

Epitope Mapping

The reason why the 3-A3-2 monoclonal antibody recovers the same interferon alpha subtype profile and composition as the polyclonal antibodies may be due to its recognition of a specific binding site, or epitope, on the interferon alpha molecule(s) that is functionally equivalent to the epitope(s) recognised by the polyclonal antibodies.

Various studies have demonstrated that some regions of interferon alpha are favoured sites for monoclonal antibody epitopes. For example, fragments 24-81 and 111-166 for the interferon alpha 1 protein (Leist and Thomas, 1984) and the fragment 107-120 interferon alpha 2 (Taylor-Papadimitriou et al., 1987) have been recognised as epitopes. It is expected that more hydrophilic regions will tend to be more exposed on external surfaces of the molecule and therefore be more available than others for binding by antibodies.

There have been previous attempts to elucidate the epitope recognised by monoclonal 3-A3-2. Kandefer-Szerszen & Lundgren, (1992) allowed monoclonal antibodies 3-A3-2, 9-1-1 and 2-2-1 to bind $^{125}$I-labelled interferon alpha 88 in solution before capturing the Monoclonal antibody-$^{125}$I-interferon alpha complex on the same antibodies coated on plates. All three monoclonals coated on plates captured all Monoclonal antibody-$^{125}$I-IFN-alpha complexes apart from the one with the same monoclonals, i.e. the epitopes recognised by each antibody are distinct. The same study also indicated that the epitope recognised by monoclonal 2-2-1 was the same as the epitope recognised by a separate, more widely studied monoclonal, NK-2.

Based on the monoclonals' abilities to bind interferon alpha variants and proteolytic fragments of interferon alpha 88, it was proposed that the epitope recognised by monoclonal 9-1-1 was centred on interferon alpha position 23, while the epitope recognised by monoclonal 2-2-1 was centred around interferon position 113. It was reported elsewhere (Viscomi et al., 1999) that monoclonal NK-2 recognises the peptide 129-141 of interferon alpha 2. That 3-A3-2 can capture 9-1-1:IFN-α88 and 2-2-1:IFN-α88 complexes indicates that the epitope recognised by 3-A3-2 is distinct from the epitope recognised by these monoclonals.

However, these data should be treated cautiously since "when a certain Monoclonal antibody was bound to interferon alpha first, it could influence (decrease or increase) the binding of the second monoclonal antibody which did not cross-react with the first monoclonal antibody" (Alkan and Braun, 1986).

The complexity of epitope mapping of interferon alpha is exemplified in studies by Viscomi and colleagues (1999). LEMonoclonal antibody-10 was shown to bind to interferon alpha 2 fragment 28-44, and could neutralise interferon alpha 2 and interferon alpha 5 activity. It could not, however, neutralise interferon alpha 21 activity even though interferon alpha 21 has the same primary sequence as interferon alpha 2 and interferon alpha 5 in positions 28-44. Thus, the sequence and/or structure of other regions of interferon alpha influence monoclonal antibody binding in this domain. Likewise, hybrid interferon alpha 8/1 was neutralised by LEMonoclonal antibody-10 even though interferon alpha 8, with which it shares its N-terminus, is not neutralised. More detailed mapping showed that residue Gly37 could be substituted with arginine but not glutamic acid without loss of LEMonoclonal antibody-10-binding. In the same way, monoclonals shown to recognise C-terminal parts of interferon alpha proteins, could bind the C-terminal domain of hybrid but not natural molecules, so the phenomenon is not restricted to a single epitope on interferon alpha.

The Viscomi study showed that certain epitopes were largely dependent on specific interferon alpha primary sequences. This is unlikely to be the case for the monoclonal 3-A3-2 epitope as the monoclonal does not recognise reduced interferon alpha 88 protein (Kandefer-Szerszen & Lundgren, unpublished), i.e., the epitope recognised by 3-A3-2 is largely a structure-dependent epitope. This will complicate interpretation of epitope mapping data as mutation of specific residues in interferon alpha may preclude binding by monoclonal 3-A3-2 owing to structural effects not directly related to the epitope recognised by the monoclonal. However, the same study showed that interferon alpha 88 was readily cleaved by trypsin at position 23, unless it was complexed with monoclonal 3-A3-2 in which case the only cleavage was at interferon alpha 88 position 50. This suggests that monoclonal 3-A3-2 occludes the trypsin cleavage site at position 23. This contradicts the finding that monoclonal 9-1-1 binds at position 23 and does not compete with monoclonal 3-A3-2 binding to interferon alpha.

Monoclonal 3-A3-2 Affinity Ligand

The inventors have shown that the 3-A3-2 monoclonal can be used as an immunoaffinity ligand in the large-scale manufacture of a human leukocyte-derived interferon alpha, and furthermore that the numbers and proportion of interferon alpha proteins eluting from such a column are within the specification for the Multiferon™ interferon alpha proteins eluting from a column of goat polyclonal antibodies. This outcome was not predicted on the basis of previous knowledge of monoclonal 3-A3-2 selectivity for interferon alpha subtype proteins, and indicates that monoclonal 3-A3-2 has utility in a process for production of a multi-subtype leukocyte interferon alpha product, especially Multiferon™. The monoclonal 3-A3-2 ligand can be manufactured more consistently and more cost-effectively than functionally equivalent goat polyclonal antibodies.

Example 1 describes work comparing the monoclonal and the polyclonal antibody in this manner. The same study also used other monoclonals as immunoaffinity ligands, particularly monoclonals 9-1-1 and NK-2. Monoclonal NK-2 failed to recover Interferon alpha 1 from culture medium, and as such is inappropriate for the Multiferon manufacturing process. Monoclonal 9-1-1 recovered all of IFN-α proteins except α8, and is therefore also inappropriate as a ligand for Multiferon® manufacture. The only monoclonal to recognise the profile of IFN-α proteins characteristic of Multiferon™, is 3-A3-2 and this was not predicted by other studies of the antibody's ability to bind IFN-α proteins (Kandefer-Szerszen & Lundgren, 1992).

Other studies have also used monoclonals coupled to beads as immunoaffinity ligands for recovery of interferon alpha proteins (but not directly compared with monoclonal 3-A3-2). LEMonoclonal antibody-10 as an immunoaffinity ligand qualitatively recovered IFN-α proteins similar to those in Multiferon™, but LYMonoclonal antibody-2 in the same study failed to recover IFN-α1 (the analyses were done by RP-HPLC, but do not include quantitation or identification of each recovered interferon alpha protein; FIGS. 1A & 2A in Viscomi et al., 1999). LEMonoclonal antibody-10 binds the N-terminal domain of some interferon alpha proteins, and can bind peptides corresponding to amino acids 28-44 of interferon alpha. However, LEMonoclonal antibody-10 does not neutralise interferon alpha 21 activity, but does neutralise interferon alpha 2 and interferon alpha 5 activities that have the same amino acid sequence in positions 28-44, i.e., factors other than this primary sequence influence the recognised epitope. Tolo and colleagues (2001) used two separate Monoclonal antibodies coupled to beads to recover IFN-alpha proteins similar to those in Multiferon™.

The major interferon alpha subtype proteins found in Multiferon™ are α1, α2, α8, α10, α14 and α21 (and possibly α17). The following are not detected in the product: IFN-α4, α5, α6, α7 and α16. Example 1 shows that typical flow-through values for the goat polyclonal column and the 3-A3-2 immunoaffinity column are less than 5%, i.e., the interferon alpha protein profile obtained after immunoaffinity chromatography is probably representative of all the interferon alpha proteins present in the culture medium. In which case, immobilised monoclonal 3-A3-2 recovers all interferon alpha subtype proteins from culture medium. This could not have been predicted from published data describing the interferon alpha protein recognition manifested by monoclonal 3-A3-2 (Kandefer-Szerszen & Lundgren, 1992). However, the proportion and identities of interferon alpha subtype proteins resulting using monoclonal 3-A3-2 in a commercially useful manufacturing process for Multiferon™ are the same as those obtained using the goat polyclonal antibody ligands.

It appears that the selectivity of monoclonal 3-A3-2 for interferon alpha subtype proteins is very much dependent on the nature of the technique being used to address the question, probably owing to the inherent flexibility of the interferon alpha molecules. Consequently, ELISA and dot-blot data that show that Monoclonal antibody 3-A3-2 differentially recognises some interferon alpha proteins have no bearing on the use of monoclonal 3-A3-2 bound to resin as an immunoaffinity ligand. However, its use in the present invention is as an immunoaffinity ligand in the Multiferon™ manufacturing process.

The available data on monoclonal 3-A3-2 as an affinity ligand indicate that it may be able to bind all interferon subtype proteins, but the specificity shown for certain 'sets' of interferon alpha proteins likely depends on the conformation of the protein molecule, caused by the nature of the situation in which the molecule is presented. Therefore, when used as an immunoaffinity ligand its conformation is such that it recognises the interferon alpha proteins present in Multiferon™.

Viscomi et al., 1999 provide an insightful comment: "The observation that the reaction between interferon molecules and interferon alpha monoclonal antibodies is sometimes unpredictable despite identity of the sequences of the region where the antigenic determinants are located stresses the importance of interferon alpha structures that can be altered by its production, preparation, formulation and storage. For this reason it is not surprising that interferon alpha from different sources (*E. coli*, lymphoblastoid cells, or leukocytes) and from different purification and formulation processes exhibit different antigenic profiles, even if the protein sequences are identical."

EXAMPLES

Example 1

Comparison Between Goat Polyclonal Antibodies and Monoclonal Antibodies to Interferon-Alpha as Immunoaffinity Ligands in the Purification of Leukocyte Interferon-Alpha One step in the purification of interferon alpha is affinity chromatography. In the current Multiferon™ process, an affinity purified polyclonal goat antibody which is coupled to cyanogen bromide-activated (CNBr-activated) Sepharose is used. If this antibody could be replaced with a monoclonal antibody with the same functional properties, the batch consistency would be more stable: goats are not cloned animals, and there is less industry experience with goat antibodies compared with monoclonal antibodies. Also leakage of antibody and antibody fragments may be less than for a polyclonal antibody as all the monoclonal antibodies would have the same binding properties.

Affinity purified monoclonal antibodies coupled to CNBr-activated Sepharose were tested. Crude leukocyte interferon alpha was applied to the immunoaffinity columns and the interferon alpha protein pattern obtained was compared with that of IFN-α recovered using the goat polyclonal antibody immunoaffinity column. The conclusion is that the 3-A3-2 monoclonal antibody gives an interferon alpha protein pattern and interferon alpha recovery similar to the interferon alpha protein pattern and interferon alpha recovery obtained with the goat polyclonal antibodies.

Materials and Methods

The antibodies were all bound to CNBr-activated Sepharose gel. The same amount and same batch of concentrated crude leukocyte interferon alpha was applied to 5 ml of each immunoaffinity column. Impurities and unbound material were removed from the column by washing with buffer. Interferon alpha was eluted with citric-acid buffer, pH2. Unbound, flow-through fractions, and eluate fractions were analysed for interferon alpha using a specific ELISA. The eluate fraction was analysed for its complement of interferon alpha proteins using reversed-phase HPLC (RP-HPLC). Interferon alpha specific activity was determined using a cytopathic protective effect assay with MDBK cells. All samples were analysed twice. The experiments were repeated with a second batch of concentrated crude leukocyte interferon alpha.

Results

In Table 2 the recovery for each experiment with every antibody coupled gel is shown. The interferon alpha protein pattern that was established with HPLC is shown in FIGS. 1 and 2.

A monoclonal antibody which binds all the interferon alpha subtype proteins that the goat polyclonal antibody binds will give batch consistency for the immunoaffinity column. Because of that, batch consistency in the purification of leukocyte IFN-alpha is also achieved. When the antibody coupled to the CNBr-Sepharose is a monoclonal, it is anticipated that leakage of antibody ligand and antibody fragments may be less than with polyclonal antibodies because each antibody molecule will have the same binding properties to the Sepharose resin.

The recovery of interferon alpha from Monoclonal antibody 3-A3-2 immunoaffinty column is as high as for polyclonal goat immunoaffinty column. The recovery from the monoclonal antibody NK2 immunoaffinty column is lower because the interferon alpha 1 and interferon alpha 21 are missing from the eluate, and presumably are not bound by the antibody. Recovery has decreased from 60% to 20% because of the fact that interferon alpha 1 is the main interferon alpha protein present in Multiferon™.

FIGS. 1 and 2 show eight reversed-phase HPLC chromatograms. The chromatograms in FIG. 1 are from one batch of concentrated crude leukocyte interferon alpha and the chromatograms in FIG. 2 are from a separate batch. The method does not allow comparison of the retention time for the individual interferon peaks. Rather, the interferon alpha protein pattern is compared to assess whether all the expected peaks are present. The RP-HPLC chromatogram for Monoclonal antibody 3-A3-2 immunoaffinity eluate contains all the interferon alpha protein peaks usually found after recovery using goat polyclonal antibody immunoaffinty column. In the chromatograms from the 9-1-1 monoclonal antibody immunoaffinty column, interferon alpha 8 is missing.

It is therefore shown that Monoclonal antibody 3-A3-2 as an immunoaffinity ligand gives an interferon alpha protein pattern and an interferon alpha recovery quantitatively similar to the interferon alpha protein pattern and interferon alpha recovery obtained with the goat polyclonal antibody immunoaffinity column.

Example 2

Production and Purification of Anti-Interferon Alpha Antibody 3-A3-2

The anti-interferon alpha monoclonal antibody 3-A3-2 is produced by mouse hybridoma cell line 3-A3-2.

The cell line has been adapted to grow in chemically defined medium. A stepwise purification process was developed for the antibody, involving an affinity step, and final formulation into carbonate buffer to permit antibody coupling to CNBr-activated Sepharose. The following describes the developed process.

Hybridoma 3-A3-2 Cultivation

Hybridoma 3-A3-2 was adapted to grow in chemically-defined medium. The hybridoma grew equally well in standard tissue culture flasks, roller bottles and stirred fermenter at 37° C. using methods common in the field. Typical antibody production by hybridoma 3-A3-2 is around 25 mg·L$^{-1}$ in batch mode.

Monoclonal Antibody 3-A3-2 Purification

Monoclonal antibody 3-A3-2 was purified from hybridoma culture medium using affinity chromatography. MEP HyperCel (BioSepra, Cat. No. 12035-028) is a Hydrophobic Charge Induction Chromatography (HCIC) Sorbent specifically designed for purification of antibodies. MEP HyperCel Columns are prepared in 50 mM Tris-HCl pH 8.0. The size of column used depends on the culture volume to be processed, but as a rule-of-thumb, 1 mL of MEP Hypercel sorbent is able to bind 3 mg of Monoclonal antibody 3-A3-2 in culture medium.

Culture material is loaded onto the sorbent at 80-100 cm/hr, then washed with equilibration buffer (10CV). Elution is performed with 0.1M Glycine pH 3.0, flow rate 40-50 cm/hr.

TFF Concentration/Diafiltration

The MEP eluate is concentrated and diafiltered into 0.1M sodium bicarbonate/0.5M sodium chloride, pH 8.3 using a Pellicon XL cassette (Millipore; Lot. No. C3CN55777), containing a regenerated cellulose, 30 kDa nominal molecular weight cut-off membrane. The membrane is equilibrated with 0.1M Glycine, pH3 before use. The feed pressure is 20-30 psi, retentate pressure (membrane pressure) 10 psi, and flux 12 ml/min. The eluate sample is concentrated, then diafiltered three times against 10 volumes of diafiltration buffer at a flux of 5 ml/min. The final 3-A3-2 antibody concentration is preferably at least 7 mg/mL.

Analysis—Murine IgG ELISA/SDS-PAGE

The amount of purified antibody during the process is determined using an ELISA specific for murine immunoglobulin.

Antibody purity is assessed by SDS-PAGE using a 5 µg load of antibody and staining the resolved gel with CBR-250 Stain.

FIG. 3 shows Monoclonal antibody 3-A3-2 purified by this scheme and analysed by SDS-PAGE. It illustrates that the non-reduced (NR) 3-A3-2 Monoclonal antibody has a mass of approximately 150 KDa expected of an intact antibody. The reduced (R) sample shows the constituent heavy and light chain bands of the expected mass.

Antibody purity is good (approx. 90%) with only a few other faint protein bands present.

Example 3

Conjugation of Monoclonal Antibody 3-A3-2 to Chromatography Resin, and Binding of IFN-Alpha Preparations In an attempt to identify the epitope on interferon alpha proteins recognised by Monoclonal antibody 3-A3-2, small scale 3-A3-2 immunoaffinity columns were produced. Different interferon alpha subtype proteins were passed through the column to determine if they were specifically bound by the immobilised antibody. The intention was to compare the primary sequence of bound interferon alphas in order to identify common determinants.

3-A3-2 Coupling to Sepharose 4B-FF

Three grams of CNBr-activated Sepharose 4B-FF (Amersham Bioscience, lot 296484) were mixed with 15 ml of cold 1 mM HCl in a 50 ml Falcon tube and rotated for 3-5 minutes. The tubes were then centrifuged at 300 rpm for 2 minutes and the supernatant fraction removed. This process is repeated.

To the swollen resin (approximately 12 ml), 12 ml of 3-A3-2 antibody (7 mg/ml in carbonate buffer, produced as described in Example 2) was added and the mixture was rotated overnight at 4° C. The excess liquid was removed after centrifugation. The resin was washed with 5 column volumes of carbonate buffer, centrifuged at 300 rpm and the supernatant fraction removed. The resin was blocked with 12 ml of 0.1M Tris-HCl, pH 8.0 for 2 hours at 4° C. A washing step was performed with 3 column volumes of 0.1M sodium acetate/0.5M NaCl pH 4.0, then 3 column volumes of 0.1M Tris-HCl/0.5M NaCl pH 8.0. This step was repeated four times and the resin stored in 20% ethanol prior to use. Coupling efficiency was analysed by SDS-PAGE to show that the antibody had coupled to the Sepharose medium.

3-A3-2 Affinity Experiments:

1 ml (50% slurry) of 3-A3-2 coupled resin was placed in a disposable polystyrene chromatography column, 0.5-2 ml bed volume (Perbio, #29920). The column was equilibrated in 0.02M Tris/0.2M NaCl/1 mM EDTA, pH 8.0.

Recombinant interferon alpha 88 (0.5 mL; solubilised and purified from *E. coli* inclusion bodies, 50-100 μg/ml; see Appendix 1) was loaded onto the 3-A3-2 immunoaffinity column, and the flow-through buffer collected. The interferon alpha 88 was allowed 15 minutes dwell-time to maximise binding by the column, then the column was washed with 5 column volumes of PBS buffer. Elution was performed with 0.1M Glycine/0.15 M NaCl, pH 2.0. Eluate fractions were buffered immediately with 1M Tris-HCl, pH 8 (0.33:1 ratio) or 0.1M NaOH (0.8:1). Samples of the load, wash and eluate fractions were analysed by SDS-PAGE, with the protein bands being silver stained (FIG. 4).

The gels in FIG. 4 indicate that recombinant interferon alpha 88 was bound by the 3-A3-2 affinity column and that it was eluted mostly in fractions 3-6. It is shown that the 3-A3-2 affinity coupling experiment was successful, and that the prepared column can bind and elute interferon alpha 88.

Published data on interferon alpha subtype protein-specificity of Monoclonal antibody 3-A3-2 indicate that it could not bind interferon alpha 2c (Andersson et al., 1991). The interferon alpha 88 (bound by Monoclonal antibody 3-A3-2, above) sequence was compared with interferon alpha 2c sequence and four variants of interferon alpha 88 were engineered to incorporate interferon alpha 2c amino acids into interferon alpha 88 (see Appendix 2 for illustration of how to produce interferon alpha variants by site-directed mutagenesis (SDM)). The interferon alpha 88 variants are:

LE49—N11S, A14T, I16M

LE50—H34R, L38F

LE51—H34R

LE52—L152F, F154L

The four interferon alpha variants (LE49, LE50, LE51 and LE52) were expressed in *E. coli*, and inclusion bodies containing the recombinant interferon alpha recovered after extraction in Bugbuster Extraction Reagent (Invitrogen) for 25 minutes. The interferon alpha variants were purified from inclusion bodies using an established method (Appendix 1). Activity of the recovered interferon alpha is determined by ELISA.

The interferon alpha variants (50-60 μg/ml; LE50 ~150 μg/ml) were passed through 3-A3-2 immunoaffinity columns as described above. In each case, the load, wash, and eluate fractions were tested for the presence of interferon alpha by SDS-PAGE.

FIG. 5 shows the SDS-PAGE gel of interferon alpha variant LE50 processed through 3-A3-2 immunoaffinity chromatography. It shows that the variant is bound by the 3-A3-2 immunoaffinity column and elutes at low pH. The same result obtains for interferon alpha variants LE49, LE51 and LE52. Immunoblots (not shown) confirm the eluate bands as interferon alpha.

Example 4

Determination of IFN-α Subtype Proteins Bound by Monoclonal Antibody 3-A3-2 Immunoaffinity Column: Epitope Mapping The results exemplified in Example 3 indicated that the reported interferon alpha subtype protein specificity of Monoclonal antibody 3-A3-2 may not be the same as that obtained for Sepharose-linked Monoclonal antibody 3-A3-2.

A broader analysis of interferon alpha-binding by Monoclonal antibody 3-A3-2 immunoaffinity column was undertaken. Multiferon™, Intron A (Recombinant IFN-α2b), twelve recombinant interferon alpha subtype proteins (purchased from PBL Biomedical Laboratories (#11000-1)), and four (selected) engineered interferon alpha variants were tested. These were passed through immobilised Monoclonal antibody 3-A3-2, with interferon alpha levels detected by a sensitive Daudi cell anti-proliferative assay.

Multiferon™ (Interferon Alfanative, lot 102C5101) and Intron A were diluted to 10,000 IU/ml with PBS prior to load. The 12 recombinant human interferon alpha proteins; α1, α2, α4, α5, α6, α7, α8, α10, α14, α16, α17 and α21, (20 000 IU) were made up to 20 000 IU/ml with sterile PBS pH 7.4.

Interferon alpha 6 (PBL Biomedical Laboratories, #11165-1) was also separately prepared at 50 000 IU/ml in sterile PBS, pH 7.4 so that it could be tested at a higher concentration to confirm earlier results.

As only small amounts of these interferon alpha proteins were available for assessment, they were run with a load of 10,000 IU. Owing to the low interferon alpha levels, the sensitive Daudi cell based anti-proliferative assay was used for assessment of interferon alpha in different fractions.

Daudi cells are maintained in RPMI 1640/10% foetal bovine serum/1-X glutaMAXI. RPMI 1640, Life technologies #32404, lot 3075960 Fbs, Life Technologies #16000-044, lot 1137907 GlutaMAXI, Life Technologies #35050-038, lot 3078606. Cells are maintained at high viability (>90%), and sub-passaged from log-phase cells, typically $<10^6$ cells/ml to $2\times10^5$ cells/ml in fresh medium. Cultures are maintained at 36.5° C./5% CO2.

Anti-proliferation experiments are done in 96-well tissue culture plates (Corning #3596). 100 μl of medium is added to each well—including penicillin/streptomycin (Sigma, #53K2338), 0.02 ml/ml medium due to non-sterile interferon alpha sample purification conditions. 100 μl of test interferon alpha sample is added to wells B2 through to H2.

Doubling dilutions are made from column 2 to column 12 by sequentially transferring 100 μl of solution from column 2 wells to column 3 wells, and to column 4 etc. 100 μl of solution is discarded from column 12 wells.

Daudi cells are prepared at approximately $4.9\times10^5$ cells/ml, and 100 μl cell suspension is added to all wells except A2-H2 which have 100 μl culture medium instead. The cells are incubated at 36.5° C./5% CO2 in a humid box for 3 days.

Relative cell density at the end of the experiment is assessed by adding 20 μl of Cell Counting Kit-8 (CCK-8; Dojindo #CK04, lot NJ616) stock solution to each 200 μl of culture in individual wells. The CCK-8 reagent is a water-soluble tetrazolium salt that produces a yellow formazan dye upon biochemical reduction in the presence of an electron carrier.

Plate absorbance is measured at 450 nm on the Dynex MRX plate reader immediately after addition of CCK-8 and at 1 hour, 3 hour and 6 hour intervals.

The A450 data are analysed to assess inhibition of Daudi cell proliferation in response to the test the interferon alpha composition.

As a control for non-specific binding by the immobilised antibody, a separate coupled antibody column was prepared. Murine anti-CD55 antibody (791T/36) was purified and concentrated to 7 mg/ml in 0.1M $NaHCO_3$/0.5M NaCl, pH 8.4 and coupled to CNBr-activated Sepharose 4B-FF following the procedure described for Monoclonal antibody 3-A3-2 in Example 3.

Interferon Proteins: Binding to 3-A3-2 Column

Anti-proliferative assay results showed that, using a 10,000 IU load, all interferon alpha subtype proteins, other than interferon alpha 6, were bound by immobilised 3-A3-2: activity measured in load samples was absent from non-binding, flow-through fractions. Owing to the low amounts of interferon alphas tested, however, no interferon alpha activity was measurable in eluate fractions to confirm that the interferon alphas had been bound and eluted by the immobilized antibody. Results in Example 3 show that at higher interferon alpha concentration, interferon alpha protein is eluted from the column. Interferon alpha 6 had some anti-proliferative activity in its non-binding, flow-through fraction indicating that it was not bound efficiently by immobilized Monoclonal antibody 3-A3-2.

Multiferon™, Intron A and interferon alpha 88 were passed through the control anti-CD55 affinity column, and anti-proliferative activity was detected in each wash fraction, indicating that lack of interferon alpha activity in the same fractions from the Monoclonal antibody 3-A3-2 column is due to specific binding of the interferon alphas by the 3-A3-2 Monoclonal antibody.

As interferon alpha 6 is the only protein apparently not bound by immobilised Monoclonal antibody 3-A3-2, this protein was retested at a higher concentration (50,000 IU/ml, 25,000 IU load). As before, anti-proliferative activity was seen in the wash fractions (and not the eluate).

Comparison of interferon alpha 6 primary sequence with other interferon alpha sequences shows that there are ten amino acid positions that are unique, the majority of these considered to be conservative (H11N(S), M15L, V60M(L), V75A, L85F, S154F/L). However, Arg80 in interferon alpha 6 is serine, threonine or aspartic acid in other interferon alpha subtype proteins, Trp105 is otherwise glycine or aspartic acid, and Gly108 is glutamic acid or aspartic acid. Two interferon alpha 88 variants were engineered (see Appendix 2):

LE60—R80S

LE61—W105G, G108E

The variants were produced as described in Appendix 1, and tested for binding by the Monoclonal antibody 3-A3-2 immunoaffinity column. Both LE60 and LE61 were bound by the immobilized antibody.

Subsequent to these results, recombinant IFN-α6 itself was prepared so that it could be tested at higher concentrations for binding by immobilised Monoclonal antibody 3-A3-2. At higher concentrations interferon alpha 6 is bound and eluted by immobilised Monoclonal antibody 3-A3-2 (analysis by SDS-PAGE and immunoblotting, not shown). These results are consistent with the affinity of Monoclonal antibody 3-A3-2 being lower for IFN-α6 than for other interferon alpha proteins.

Conclusion

Twelve recombinant interferon alpha subtype proteins, Multiferon™, Intron A, IFN-alpha88 and five recombinant interferon alpha variants, have been passed through immobilised Monoclonal antibody 3-A3-2. Only one interferon alpha protein, interferon alpha 6, is not bound by 3-A3-2, and this only when interferon alpha 6 is tested at very low concentrations: it is bound at higher concentrations. These results suggest that immobilised Monoclonal antibody 3-A3-2 binds all human interferon alphas, but has not yet allowed identification of the recognised epitope.

Example 5

Pilot Scale Comparison of Monoclonal Antibody 3-A3-2 and Goat Antibodies for Production of Multiferon™

The present purification process for Multiferon™ involves an immunoaffinity chromatography step where polyclonal antibodies from goats are used as ligands. As herein described, a preferred process would use monoclonal antibodies. These are produced using a master cell bank, which can be characterised with respect to adventitious agent contamination. Also, the produced monoclonal antibodies have a higher batch consistency compared to the polyclonal antibodies.

During the work done to characterise Multiferon™, the major interferon alpha protein subtypes in the final purified product pre-formulation, were identified using amino acid sequencing, and the interferon alpha proteins identified were α-1, α-2, α-8, α-10, α-14 and α-21. The other interferon alpha subtypes were either not present or present at concentrations below the detection limit of the method. According to the literature, as many as nine different interferon alpha subtype proteins have been found when human leukocytes are induced using Sendai virus (Nyman et al). Here α-1, α-2, α-4, α-7, α-8, α-10, α-14, α-17 and α-21 were identified using a variety of analytical techniques such as mass spectrometry and amino acid sequencing.

This study was undertaken with the purpose of investigating the possibility to substitute the current immunoaffinity ligand, i.e. the polyclonal goat antibody with a monoclonal murine antibody. To be able to change the manufacturing process, the quality and composition of the purified interferon must not change. Different batches of concentrated crude interferon were purified using both types of ligands and the quality of the purified material was analysed using a battery of tests.

In addition, an accelerated stability study of the purified interferon using the monoclonal and polyclonal antibodies respectively was performed.

Materials and Methods

Different batches of concentrated crude interferon were purified using the ÄKTA Explorer pilot-scale purification process. All work was done according to the batch record (Viranative, doc no RD-01) except for the different immunoaffinity columns used (see below).

Immunoaffinity Columns:

3-A3-2: The monoclonal immunoaffinity column was prepared by a coupling reaction between 7 mg Monoclonal antibody 3-A3-2/mL CNBr-activated Sepharose FF. The Monoclonal antibody was obtained from Viragen (Scotland) Ltd., 2003 Aug. 13. 110 ml affinity gel was prepared, and the coupling recovery was 89%. The interferon capacity was determined to be 22.5 MIU/ml gel.

Goat polyclonal: The immunoaffinity gel RS 6134-6141 was used as a reference. This gel was prepared in May 2002 and had a capacity of 11.3 MIU/mL in February 2003.

Concentrated Crude Interferon:

Several batches of concentrated crude interferon of different origin were used. Batch no K-543 produced in the ordinary manufacturing process (produced 2000-12-15) and stored for four years below −15° C. was used for experiment number P-428, P-429 and P-430. Concentrated crude interferon from laboratory fermenters was also used (P-435 batch no TJ-133-046 and P-434 TJ-133-049).

Analysis:

The purified interferon was analysed using the analytical procedures listed below that form the Quality Control release criteria for Multiferon™:

Determination of Ovalbumin Content

SDS-PAGE, Silver stain

SDS-PAGE, Coomassie Brilliant Blue

RP-HPLC

Bioassay MDBK

Determination of Ovalbumin

The ovalbumin content is determined by using an ELISA with plates coated with goat-anti ovalbumin. A secondary antibody is added (Rabbit-anti-Ovalbumin). Alkaline phosphatase-labelled goat-anti-rabbit-Ig is used as a conjugate. The amount of colour developed is directly proportional to the amount of ovalbumin in the sample.

SDS-PAGE, CBB

The CBB method is chosen for the purity analysis, mainly because with this method proteins stain more equally, and densitometric analysis of CBB stained gels is therefore expected to give results that reflect the actual purity in terms of presence of non interferon alpha proteins in the preparation of Multiferon™.

RP-HPLC

The interferon alpha protein pattern is resolved by reversed phase high performance liquid chromatography (RP-HPLC). RP-HPLC is a chromatographic method with high resolving power. The stationary phase in the separating column consists of small uniform particles of surface-modified silica. Proteins or other molecules interact with the stationary phase through hydrophobic interactions. They can be selectively eluted from the column by increasing the amount of organic modifier (acetonitrile) in the mobile phase. A silica with coupled C4 (butyl) groups had been found to be useful for the separation of interferon alpha proteins.

SDS-PAGE, Silver Stain

SDS-PAGE with subsequent silver staining is used to monitor degradation of interferon proteins.

A reference preparation is analysed in parallel with the sample. Degradation will be detected as loss of bands or appearance of smaller protein fragments not present in the reference.

Determination of Biological Activity

A biological test method was used to determine activity of the preparation and this method was calibrated against the international reference preparation 69/19, now replaced by the international WHO standard 94/784. Madin Darby Bovine Kidney cells are added to different dilutions of the sample. The antiviral activity is defined as the ability to protect the cells against the cytopathic effect of vesicular stomatitis virus (VSV). The biological activity is expressed as International Units per millilitre.

Accelerated Stability Study.

The stability of the purified material was tested by incubation at room temperature for 6 weeks. After 6 weeks incubation batches P429, P430, P434 and P435 show a SDS-PAGE silver stain pattern that is similar to the "start-values", i.e. there is no instability indication. It should be noted that the interferon has been stored in small glass vials, not the usual containers used for Multiferon™.

Results and Discussion

In Table 3, a comparison using concentrated crude interferon produced in 2000 is shown. The yield and quality of the purified interferon alpha is similar for the polyclonal and monoclonal purification process. When analysed using SDS-PAGE silver stain, the interferon alpha products are identical.

As can be seen in FIG. 6, the interferon alpha protein pattern looks similar for the monoclonal and polyclonal antibody. All major interferon alpha protein peaks can be found using the monoclonal as a ligand.

When concentrated crude interferon produced in laboratory fermenters is purified, similar results are observed (see Table 4).

Before it can be confirmed that the interferon alpha protein pattern is equal, additional analysis must be performed. UV-absorption is relatively insensitive and the interferon alpha protein peaks are not fully resolved. There is a risk that a minor component can be lost and not discovered using only RP-HPLC.

Initial data indicate that interferon alpha recovered using Monoclonal antibody 3-A3-2 is as stable as the same interferon alpha protein mixture recovered on the goat polyclonal antibody column.

These experiments indicate that there is no difference between the purified leukocyte interferon alpha composition produced using the 3-A3-2 monoclonal antibody when compared to the goat derived polyclonal antibody mix, particularly with regard to the proportion and yield of interferon alpha protein subtype recovery.

APPENDIX 1

Extraction of Recombinant Interferon Alpha from *E. coli*

Recombinant interferon alpha was extracted from *E. coli* pellets by mixing with the appropriate volume (1 g=5 ml) of Bugbuster Extraction Reagent (Invitrogen) for 25 minutes. The preparation was centrifuged and the soluble fraction discarded. To the pellet, 7.5M Guanadine-HCl (volume varies relative to pellet size) was added and allowed to dissolve, then, 4 volumes of 0.04M Tris/1 mM EDTA, pH 8.0 was added, and 30% PEG 6000 added to a final concentration of 3% PEG 6000. The preparation was agitated at 4° C. for 30 minutes then centrifuged. The supernatant fraction was desalted through a HiPrep 26/10 desalting column (Amersham Bioscience, lot No. 302289), and buffer exchanged by running 0.04M Tris/1 mM EDTA, pH8.0 through at 113 cm/hr.

The eluate was passed through a 5 ml Anion Exchange column (DEAE) in Tris buffer pH8.0 (152 cm/hr) and washed until the UV-absorbance was stable. The interferon was eluted with 0.02M Tris/1 mM EDTA/0.2M NaCl pH 8.0 (152 cm/hr) and the fractions analysed for interferon alpha protein by SDS-PAGE with CBR-250 staining.

APPENDIX 2

Construction and Expression of Interferon Alpha Variants to Determine Location of Recognised Epitope The source of all the bacterially-derived recombinant interferon alphas used for this work was the plasmid pIFNα88NC-P6 and the bacterial strain W3110, both obtained from Erik Lundgren, Umea University, Sweden. The plasmid pIFNα88NC-P6 contains the interferon alpha coding sequence placed under the control of phage lambda leftward facing promoter (PL), expression from which can be regulated by the addition of exogenous tryptophan. Recombinant interferon alpha 88 expressed using this system is the antigen against which goat polyclonal antibodies are raised, the same polyclonal antibodies are used in the production of Multiferon™.

The first stage was to verify the identity of the interferon alpha coding sequence contained in pIFNα88NC-P6. Because of the low copy number on in the pBR322 backbone of this plasmid it was not possible to sequence the interferon alpha 88 insert directly. Therefore, almost the entire coding sequence was amplified by PCR using the primers MUT5 (5'

TgA TCT gCC TCA gAC CCA 3') (SEQ ID NO: 3) and MUT3 (5' TCA ATC CTT ACg ACg TAA TC 3') (SEQ ID NO: 4), and cloned into a commercially available plasmid, pGEMTeasy (Promega, San Luis Obispo, Calif.). The full DNA sequence and predicted primary amino acid sequence of the cloned PCR product is shown in FIG. 7. Primer positions are in bold text, and amino acid numbers are given in brackets at end of each line.

These sequence data also confirm the successful mutagenesis carried out in Umea to alter two arginine doublets, residues 12 and 13, 163 and 164 from AggAgg to CgTCgT). These changes were introduced to reflect codon bias in *E. coli*.

The successful and regulatable expression of recombinant interferon alpha 88 from this plasmid was verified by immunoblotting and ELISA analysis. As such pIFNα88NC-P6 was used as the basis for engineering all future variants.

APPENDIX 3

Mutagenesis

Two categories of amino acids were identified as being targets for mutagenesis. First, the alteration of key residues in interferon alpha 88 to those amino acids in equivalent positions in interferon alpha 2. The QuikChangeα Site-Directed Mutagenesis Kit (Stratagene, La Jolla, Calif.) was used to generate four separate alpha88/alpha2 hybrid molecules pLE49; N11S, A14T and I16M, pLE50; H34R and L38F, pLE51, H34R only and pLE52; L152F and F154L. One oligonucleotide pair was used to introduce each subset of mutations, oligonucleotides A1 and A1 comp to create pLE49, AB2 and AB2comp to create pLE50, AB2A and AB2Acomp to create pLE51 and E1 and E1comp to create pLE52.

```
                                        (SEQ ID NO:5)
A1          CCTgggTAgCCgTCgTACCTTgATgCTCCTggCA (SEQ ID NO:6)
A1comp      TgCCAggAgCATCAAggTACgACggCTACCCAgg (SEQ ID NO:7)
AB2         ggACAgACgTgACTTTggATTTCCCCAggAg (SEQ ID NO:8)
AB2comp     CTCCTggggAAATCCAAAgTCACgTCTgTCC (SEQ ID NO:9)
AB2A        ggACAgACgTgACTTTggACTTCCCCAggAg (SEQ ID NO:10)
AB2Acomp    CTCCTggggAAgTCCAAAgTCACgTCTgTCC (SEQ ID NO:11)
E1          gCAgAAATCATgAgATCCTTTTCTTTgTCAACAAAC (SEQ ID NO:12)
E1comp      gTTTgTTgACAAAgAAAAggATCTCATgATTTCTgC
```

Second, on the basis that there are significant primary sequence differences between IFN-alpha88 and interferon alpha 6 two alpha88/alpha6 hybrid molecules were also created; pLE60 with the S80R mutation and pLE61 with both the G105W and E108G mutations. One oligonucleotide pair was used to generate each new plasmid; eightmutS (5' TCT gCT gCT Tgg gAA Cag CgT CTC CTA gAA AAA TTT TCC 3') (SEQ ID NO: 13) and eightmutAS (5' ggA AAA TTT TTC TAg gAg Acg CTg TTC CCA AgC AgC AgA 3') (SEQ ID NO: 14) for pLE60 and oneofemutS (5' ATA Cag gAg gTT Tgg Atg gAA ggC ACT CCC CTg Atg 3') (SEQ ID NO: 15) and oneofemutAS (5' CAT Cag ggg AgT gCC TTC CAT CCA AAC CTC CTg TAT 3') (SEQ ID NO: 16) for pLE61.

As before, because pLE49-52 and 60, 61 are all low copy number plasmids direct sequencing was not possible. Therefore the MUT5 and MUT3 primer pair were used to amplify coding sequences from candidate mutagenesis clones and cloned into pGEMTeasy. These samples were sequenced and positive clones identified. DNA sequencing results indicated that the mutagenesis had been completed with 100% efficiency.

The predicted amino acid sequences of pLE60 and pLE61 are shown in FIGS. **8*a* and 8*b***, altered amino acids are shown in bold text.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

REFERENCES

Adolf, G. R. et al. J. Interferon Res. 10 (Suppl. 1) 557
Alkan, S. S. and Braun, D. G. 1986 Ciba Foundation Symposium 119 264-278
Altschul, et al. J. Mol. Biol. 215:403-410
Altschul et al. Nucleic Acids Res. 25:3389-3402
Andersson, G., Lundgren, E. and Ekre, H-P, T. J Interferon Res. 11 53-60.
Antonelli G et al., J Infectious Diseases 163 882-5
Ausubel et al, Short Protocols in Molecular Biology, John Wiley and Sons
Berg, K. 1984 J. Interferon Res. 4 481-491
Berg T et al. Am J Gastroenterol 96(2) 612-4
Bird et al. Science 242:423-426
Bodanzsky, M. and Bodanzsky, A. The Practice of Peptide Synthesis, Springer Verlag, New York
Cantell, K. et al., Methods in Enzymology 78 499-505
Golovleva, I et al., Am J Hum Genet 59:570-8.
Hollinger, P. et al. PNAS 90:6444-6448
Huston et al. PNAS USA 85:5879-5883
Jacobs, S J et al., J Biol Response Mod 7:447-456
Kandefer-Szerszen, M and Lundgren, E. Arch. Immunol. Ther. Exp. 40 241-246
Karlin and Altschul Proc. Natl. Acad. Sci. USA 87:2264-2268
Karlin and Altschul Proc. Natl. Acad. Sci. USA 90:5873-5877
Leist, T and Thomas, R. M. Biochemistry 23(12) 2541-2547
Liao. M J et al., J Infect Dis 165:757-760
Lok, A S et al., Hepatology 12:1266-1270
Lund, B., J. Interferon Res. 5(2) 229-238
Merup M et al., Eur J Cancer 30 1729-1730
Nyman, T. A. et al.,' Biochem. J. 329 295-302
Pearson & Lipman Proc. Natl. Acad. Sci. 85:2444-8
Pestka S et al. 'Interferons and their actions' 56 727-777
Plückthun, Bio/Technology 9:545-551
Pohl, G., J. Interferon Res. 14 (Suppl. 1). S63
Reff, Curr. Opinion Biotech. 4:573-576
Sambrook et al., "Molecular Cloning", A Laboratory Manual, Cold Spring Harbor Laboratory Press
Secher D S, Burke D C 1980 'Nature. 285 446-450.
Staehelin T et al., Tex Rep Biol Med. 41 43-58.
Staehelin T et al. Proc Natl Acad Sci USA. 78(3)1848-52.
Stewart, J. M. and Young, J. D. Solid Phase Peptide Synthesis, 2nd edition, Pierce Chemical Company, Rockford, Ill.

Taylor-Papadimitriou, J. et al. J. Immunol. 139(10) 3375-3381
Tolo, H. et al. J. Interferon Cytokine Research 21 913-920
Torellis & Robotti Comput. Appl. Biosci., 10:3-5
Trill et al., Curr. Opinion Biotech. 6:553-560
Tsuki, K. et al. Microbiol. Immunol. 30 (11) 1129-1139
Viscomi, G. C. et al. J. Int. Cytokine Res. 19 319-326
von Wussow P et al. Blood 78 38-43
Ward, E. S. et al. Nature 341:544-546
Weck, P K et al., J Interferon Res 9 (Suppl 1):S37-43

TABLE 1

Subtype proportions prescribed for Multiferon

| | Group 1 (Alpha 14) | Group 2 (Alpha 2, Alpha 21) | Group 3 (Alpha 10, Alpha 8) | Group 4 (Alpha 1) |
|---|---|---|---|---|
| Limits (%) | 11 +/− 3 | 30 +/− 7 | 22 +/− 6 | 37 +/− 9 |

TABLE 2

Efficiency of recovery of leukocyte interferon-alpha by immunoaffinity chromatography using four separate antibody ligands

| antibody | Flow-through (%) | eluate (IU) | recovery (%) |
|---|---|---|---|
| polyclonal | 2 | 17.34 | 69 |
| | 2 | 13.94 | 49 |
| mononclonal 3-A3-2 | 1 | 16.49 | 66 |
| | 5 | 17.00 | 61 |
| mononclonal 9-1-1 | <1 | 14.41 | 58 |
| | 5 | 5.50 | 20 |
| monoclonal NK-2 | 37 | 5.53 | 22 |
| | 65 | 6.20 | 22 |

TABLE 3

Comparison using concentrated crude interferon batch no K-543

| Exp. no. | Immunoaffinity ligand | Conc RIFN MIU | yield % | Eluate IFN-α pattern % | IFN-α-Purified purity % | ovalbumin ng/ml | IFN-α pattern % | SDS page silver |
|---|---|---|---|---|---|---|---|---|
| P-429 | 3A32 Ab | 1033.6 | 73 | 11.0 | 48 | >98.7 | <1.7 | 12.2 | Red. complies |
| | | | | 31.1 | | | | 32.0 | |
| | | | | 23.6 | | | | 21.6 | |
| | | | | 34.3 | | | | 34.1 | |
| P-428 | polyclonal Ab | 855.7 | 74 | 11.3 | 52 | — | — | 11.5 | — |
| | | | | 27.8 | | | | 28.8 | |
| | | | | 26.7 | | | | 25.0 | |
| | | | | 34.1 | | | | 34.7 | |
| P-430 | polyclonal Ab | 960.8 | 84 | 10.9 | 44 | — | — | 10.8 | Red. complies |
| | | | | 24.7 | | | | 27.6 | |
| | | | | 29.6 | | | | 30.4 | |
| | | | | 34.8 | | | | 31.2 | |

Bold text - Out of specification
Limit IFN-α pattern: group 1. 11 ± 3, group 2. 30 ± 7, group 3. 22 ± 6, group 4. 37 ± 9

TABLE 4

Comparison using concentrated crude interferon produced in lab fermenters (batch no TJ-133-049 and TJ-133-046)

| Exp. no | Immunoaffinity ligand | Conc RIFN MIU | yield % | Eluate IFN-α pattern % | IFN-α-Purified purity % | IFN-α pattern % | SDS page silver |
|---|---|---|---|---|---|---|---|
| P-434 | 3A32 Ab | 375.6 | 70 | 12.5 | 42 | — | 13.0 | Red: Extra band between IFN bands. Shadows under. |
| | | | | 28.8 | | | 30.2 | |
| | | | | 21.0 | | | 27.5 | |
| | | | | 37.7 | | | 29.3 | |

TABLE 4-continued

Comparison using concentrated crude interferon produced in lab fermenters (batch no TJ-133-049 and TJ-133-046)

| Exp. no | Immunoaffinity ligand | Conc RIFN MIU | Eluate yield % | Eluate IFN-α pattern % | IFN-α-Purified yield purity % | IFN-α-Purified pattern % | SDS page silver |
|---|---|---|---|---|---|---|---|
| P-435 | polyclonal Ab | 1007 | 85 | 10.4<br>23.7<br>29.2<br>36.7 | 52 | 10.3<br>25.8<br>33.5<br>30.3 | Red: Extra band between IFN bands. Shadows under. |

Bold text - Out of specification
Red - reduced conditions
Non-red - non-reducing conditions
Limit IFN-α pattern: group 1. 11 ± 3, group 2. 30 ± 7, group 3. 22 ± 6, group 4. 37 ± 9

---

The invention claimed is:

1. A method of purifying a human multi-subtype interferon alpha composition, the method comprising the steps of:
    contacting crude interferon with the monoclonal antibody 3-A3-2 or a binding fragment thereof bound to a solid support,
    eluting the adsorbed interferon from said support, and
    recovering a multi-subtype interferon alpha composition comprising interferon alpha proteins of subtypes alpha 1, alpha 2, alpha 8, alpha 10, alpha 14 and alpha 21 from the eluted interferon.

2. A method as claimed in claim 1 wherein the monoclonal antibody is secreted by the hybridoma cell line having the accession number ECACC 05030201.

3. A method as claimed in claim 1 wherein the monoclonal antibody or binding fragment thereof has a heavy chain variable region amino acid sequence of SEQ ID NO: 1.

4. A method as claimed in claim 1 wherein the monoclonal antibody or binding fragment thereof has a light chain variable region amino acid sequence of SEQ ID NO:2.

5. A method as claimed in claim 1 wherein the monoclonal antibody or binding fragment thereof comprises a heavy chain amino acid sequence of SEQ ID NO:1 and a light chain variable amino acid sequence of SEQ ID NO:2.

6. A method as claimed in claim 1 wherein the solid support comprises a matrix selected from the group consisting of an agarose bead, a polystyrene bead, a silica bead, a chelating agarose bead, and a magnetic bead.

7. A method as claimed in claim 1 wherein the antibody is bound to carbohydrate, glass, silicon or another antibody.

8. A method as claimed in claim 1 wherein the antibody is bound to cyanogen bromide-activated agarose.

9. A method as claimed in claim 1 wherein the antibody is joined to the support through a linker.

10. A method as claimed in claim 1 wherein the purified multi-subtype interferon alpha composition contains interferon alpha subtype proteins at the following proportions by weight: interferon alpha 1 at 37+/−9%, alpha 2 plus alpha 21 at 30+/−7%, alpha 8 plus alpha 10 at 22+/−6%, and alpha 14 at 11+/−3%.

11. A process for the purification of a crude human leukocyte interferon, said process comprising the steps of:
  (a) passing a solution of crude interferon through an immunoaffinity adsorption column, said column having monoclonal antibody 3-A3-2 or a binding fragment thereof bound to a solid support;
  (b) eluting antibody bound interferon alpha from the column using a buffer solution;
  (c) purifying the eluate by either precipitation or by ion exchange chromatography; and
  (d) recovering the precipitated, or ion exchange-concentrated, interferon alpha composition obtained in step (c) comprising interferon alpha proteins of subtypes alpha 1, alpha 2, alpha 8, alpha 10, alpha 14 and alpha 21.

12. The process of claim 11 wherein the monoclonal antibody or binding fragment thereof is derived from the hybridoma cell line having the accession number ECACC 05030201.

13. The process of claim 11 wherein the antibody or binding fragment thereof has a heavy chain variable region amino acid sequence of SEQ ID NO:1.

14. The process of claim 11 wherein the antibody or binding fragment thereof has a light chain variable region amino acid sequence of SEQ ID NO:2.

15. The process of claim 11 wherein the antibody or binding fragment thereof comprises a heavy chain amino acid sequence of SEQ ID NO:1 and a light chain variable amino acid sequence of SEQ ID NO:2.

16. The process of claim 11 which further comprises the step of purifying the eluate from the immunoaffinity adsorption column using an ion exchange column.

17. The process of claim 11 wherein the precipitation of step (c) comprises a further secondary precipitation step, Wherein the interferon resulting from this secondary precipitation step is further precipitated in ethanol prior to its recovery.

18. The process as claimed in claim 11 wherein the precipitate is further subject to gel filtration, with effluent fractions having absorbance at 280 nm being collected and recovered.

* * * * *

SEQUENCE LISTING

<160> NUMBER OF SEQ ID NOS: 20

<210> SEQ ID NO 1
<211> LENGTH: 120
<212> TYPE: PRT
<213> ORGANISM: Murine

<400> SEQUENCE: 1

Gln Val Gln Leu Gln Glu Ser Gly Thr Val Leu Ala Arg Pro Gly Ala
1               5                   10                  15

Ser Val Lys Met Ser Cys Lys Ala Ser Gly Tyr Ser Phe Thr Thr Tyr
            20                  25                  30

Trp Met His Trp Val Lys Gln Arg Pro Gly Gln Gly Leu Glu Trp Ile
        35                  40                  45

Gly Val Ile Tyr Pro Gly Asn Gly Asp Thr Thr Tyr Asn Gln Lys Phe
    50                  55                  60

Lys Asp Lys Ala Lys Leu Thr Ala Val Thr Ser Ala Asn Thr Ala Tyr
65                  70                  75                  80

Met Glu Leu Ser Ser Leu Thr Asn Glu Asp Ser Ala Val Tyr Phe Cys
                85                  90                  95

Thr Arg Asn Tyr Lys Tyr Asp Tyr Tyr Thr Met Asp Tyr Trp Gly Gln
                100                 105                 110

Gly Thr Thr Val Thr Val Ser Ser
            115                 120

<210> SEQ ID NO 2
<211> LENGTH: 111
<212> TYPE: PRT
<213> ORGANISM: Murine

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly His Ser Tyr Met His Trp Tyr Gln Gln Lys Pro Gly Gln Thr Pro
        35                  40                  45

```
Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Gly
                 85                  90                  95

Glu Leu Pro Phe Thr Phe Gly Ser Gly Thr Lys Leu Glu Ile Lys
            100                 105                 110

<210> SEQ ID NO 3
<211> LENGTH: 18
<212> TYPE: DNA
<213> ORGANISM: Artificial
<220> FEATURE:
<223> OTHER INFORMATION: Chemically synthesized primer MUT5

<400> SEQUENCE: 3
tgatctgcct cagaccca                                                18

<210> SEQ ID NO 4
<211> LENGTH: 20
<212> TYPE: DNA
<213> ORGANISM: Artificial
<220> FEATURE:
<223> OTHER INFORMATION: Chemically synthesized primer MUT3

<400> SEQUENCE: 4
tcaatcctta cgacgtaatc                                              20

<210> SEQ ID NO 5
<211> LENGTH: 34
<212> TYPE: DNA
<213> ORGANISM: Artificial
<220> FEATURE:
<223> OTHER INFORMATION: Chemically synthesized Oligonucleotide A1

<400> SEQUENCE: 5
cctgggtagc cgtcgtacct tgatgctcct ggca                              34

<210> SEQ ID NO 6
<211> LENGTH: 34
<212> TYPE: DNA
<213> ORGANISM: Artificial
<220> FEATURE:
<223> OTHER INFORMATION: Chemically synthesized oligonucleotide A1comp

<400> SEQUENCE: 6
tgccaggagc atcaaggtac gacggctacc cagg                              34

<210> SEQ ID NO 7
<211> LENGTH: 31
<212> TYPE: DNA
<213> ORGANISM: Artificial
<220> FEATURE:
<223> OTHER INFORMATION: Chemically synthesized oligonucleotide AB2

<400> SEQUENCE: 7
ggacagacgt gactttggat ttccccagga g                                 31

<210> SEQ ID NO 8
<211> LENGTH: 31
<212> TYPE: DNA
<213> ORGANISM: Artificial
<220> FEATURE:
<223> OTHER INFORMATION: Chemically synthesized oligonucleotide AB2comp
```

```
<400> SEQUENCE: 8
ctcctgggga aatccaaagt cacgtctgtc c                                    31

<210> SEQ ID NO 9
<211> LENGTH: 31
<212> TYPE: DNA
<213> ORGANISM: Artificial
<220> FEATURE:
<223> OTHER INFORMATION: Chemically synthesized oligonucleotide AB2A

<400> SEQUENCE: 9
ggacagacgt gactttggac ttccccagga g                                    31

<210> SEQ ID NO 10
<211> LENGTH: 31
<212> TYPE: DNA
<213> ORGANISM: Artificial
<220> FEATURE:
<223> OTHER INFORMATION: Chemically synthesized oligonucleotide AB2Acomp

<400> SEQUENCE: 10
ctcctgggga agtccaaagt cacgtctgtc c                                    31

<210> SEQ ID NO 11
<211> LENGTH: 36
<212> TYPE: DNA
<213> ORGANISM: Artificial
<220> FEATURE:
<223> OTHER INFORMATION: Chemically synthesized oligonucleotide E1

<400> SEQUENCE: 11
gcagaaatca tgagatcctt ttctttgtca acaaac                               36

<210> SEQ ID NO 12
<211> LENGTH: 36
<212> TYPE: DNA
<213> ORGANISM: Artificial
<220> FEATURE:
<223> OTHER INFORMATION: Chemically synthesized oligonucleotide E1comp

<400> SEQUENCE: 12
gtttgttgac aaagaaaagg atctcatgat ttctgc                               36

<210> SEQ ID NO 13
<211> LENGTH: 39
<212> TYPE: DNA
<213> ORGANISM: Artificial
<220> FEATURE:
<223> OTHER INFORMATION: Chemically synthesized oligonucleotide
      eightmutS

<400> SEQUENCE: 13
tctgctgctt gggaacagcg tctcctagaa aaatttttcc                           39

<210> SEQ ID NO 14
<211> LENGTH: 39
<212> TYPE: DNA
<213> ORGANISM: Artificial
<220> FEATURE:
<223> OTHER INFORMATION: Chemically synthesized oligonucleotide
      eightmutAS

<400> SEQUENCE: 14
ggaaaatttt tctaggagac gctgttccca agcagcaga                            39
```

<210> SEQ ID NO 15
<211> LENGTH: 36
<212> TYPE: DNA
<213> ORGANISM: Artificial
<220> FEATURE:
<223> OTHER INFORMATION: Chemically synthesized oligonucleotide oneofemutS

<400> SEQUENCE: 15
atacaggagg tttggatgga aggcactccc ctgatg                         36

<210> SEQ ID NO 16
<211> LENGTH: 36
<212> TYPE: DNA
<213> ORGANISM: Artificial
<220> FEATURE:
<223> OTHER INFORMATION: Chemically synthesized oligonucleotide oneofemutAS

<400> SEQUENCE: 16
catcagggga gtgccttcca tccaaacctc ctgtat                         36

<210> SEQ ID NO 17
<211> LENGTH: 499
<212> TYPE: DNA
<213> ORGANISM: Artificial
<220> FEATURE:
<223> OTHER INFORMATION: cloned PCR product from the bacterially-derived recombinant plasmid pIFNalpha88NC-P6
<220> FEATURE:
<221> NAME/KEY: CDS
<222> LOCATION: (2)..(499)

<400> SEQUENCE: 17

```
t gat ctg cct cag acc cac agc ctg ggt aat cgt cgt gcc ttg ata ctc      49
  Asp Leu Pro Gln Thr His Ser Leu Gly Asn Arg Arg Ala Leu Ile Leu
  1               5                  10                  15 ctg gca caa atg gga aga att tct cct ttc tcc tgc ctg aag gac aga        97
Leu Ala Gln Met Gly Arg Ile Ser Pro Phe Ser Cys Leu Lys Asp Arg
            20                  25                  30 cat gac ttt gga ctt ccc cag gag gag ttt gat ggc aac cag ttc cag       145
His Asp Phe Gly Leu Pro Gln Glu Glu Phe Asp Gly Asn Gln Phe Gln
        35                  40                  45 aag act caa gcc atc tct gtc ctc cat gag atg atc cag cag acc ttc       193
Lys Thr Gln Ala Ile Ser Val Leu His Glu Met Ile Gln Gln Thr Phe
    50                  55                  60 aat ctc ttc agc aca gag gac tca tct gct gct tgg gaa cag agc ctc       241
Asn Leu Phe Ser Thr Glu Asp Ser Ser Ala Ala Trp Glu Gln Ser Leu
65                  70                  75                  80 cta gaa aaa ttt tcc act gaa ctt tac cag caa ctg aat aac ctg gaa       289
Leu Glu Lys Phe Ser Thr Glu Leu Tyr Gln Gln Leu Asn Asn Leu Glu
                85                  90                  95 gca tgt gtg ata cag gag gtt ggg atg gaa gag act ccc ctg atg aat       337
Ala Cys Val Ile Gln Glu Val Gly Met Glu Glu Thr Pro Leu Met Asn
            100                 105                 110 gag gac tcc atc ctg gct gtg agg aaa tac ttc caa aga atc act ctt       385
Glu Asp Ser Ile Leu Ala Val Arg Lys Tyr Phe Gln Arg Ile Thr Leu
        115                 120                 125 tat cta aca gag aag aaa tac agc cct tgt gcc tgg gag gtt gtc aga       433
Tyr Leu Thr Glu Lys Lys Tyr Ser Pro Cys Ala Trp Glu Val Val Arg
    130                 135                 140
```

```
gca gaa atc atg aga tcc ctc tct ttt tca aca aac ttg caa aaa aga     481
Ala Glu Ile Met Arg Ser Leu Ser Phe Ser Thr Asn Leu Gln Lys Arg
145                 150                 155                 160 tta cgt cgt aag gat tga                                             499
Leu Arg Arg Lys Asp
                165
```

<210> SEQ ID NO 18
<211> LENGTH: 165
<212> TYPE: PRT
<213> ORGANISM: Artificial
<220> FEATURE:
<223> OTHER INFORMATION: predicted primary amino acid sequence of cloned
      PCR product from the bacterially-derived recombinant plasmid
      pIFNalpha88NC-P6

<400> SEQUENCE: 18

```
Asp Leu Pro Gln Thr His Ser Leu Gly Asn Arg Arg Ala Leu Ile Leu
1               5                   10                  15

Leu Ala Gln Met Gly Arg Ile Ser Pro Phe Ser Cys Leu Lys Asp Arg
                20                  25                  30

His Asp Phe Gly Leu Pro Gln Glu Glu Phe Asp Gly Asn Gln Phe Gln
            35                  40                  45

Lys Thr Gln Ala Ile Ser Val Leu His Glu Met Ile Gln Gln Thr Phe
        50                  55                  60

Asn Leu Phe Ser Thr Glu Asp Ser Ser Ala Ala Trp Glu Gln Ser Leu
65                  70                  75                  80

Leu Glu Lys Phe Ser Thr Glu Leu Tyr Gln Gln Leu Asn Asn Leu Glu
                85                  90                  95

Ala Cys Val Ile Gln Glu Val Gly Met Glu Glu Thr Pro Leu Met Asn
            100                 105                 110

Glu Asp Ser Ile Leu Ala Val Arg Lys Tyr Phe Gln Arg Ile Thr Leu
        115                 120                 125

Tyr Leu Thr Glu Lys Lys Tyr Ser Pro Cys Ala Trp Glu Val Val Arg
    130                 135                 140

Ala Glu Ile Met Arg Ser Leu Ser Phe Ser Thr Asn Leu Gln Lys Arg
145                 150                 155                 160

Leu Arg Arg Lys Asp
                165
```

<210> SEQ ID NO 19
<211> LENGTH: 166
<212> TYPE: PRT
<213> ORGANISM: Artificial
<220> FEATURE:
<223> OTHER INFORMATION: predicted amino acid sequent of pLE60

<400> SEQUENCE: 19

```
Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
                20                  25                  30

Arg His Asp Phe Gly Leu Pro Gln Glu Glu Phe Asp Gly Asn Gln Phe
            35                  40                  45

Gln Lys Thr Gln Ala Ile Ser Val Leu His Glu Met Ile Gln Gln Thr
        50                  55                  60

Phe Asn Leu Phe Ser Thr Glu Asp Ser Ser Ala Ala Trp Glu Gln Arg
65                  70                  75                  80
```

-continued

```
Leu Leu Glu Lys Phe Ser Thr Glu Leu Tyr Gln Gln Leu Asn Asn Leu
                85                  90                  95

Glu Ala Cys Val Ile Gln Glu Val Gly Met Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 20
<211> LENGTH: 166
<212> TYPE: PRT
<213> ORGANISM: Artificial
<220> FEATURE:
<223> OTHER INFORMATION: predicted amino acid sequence of pLE61

<400> SEQUENCE: 20

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Leu Pro Gln Glu Glu Phe Asp Gly Asn Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asn Leu
                85                  90                  95

Glu Ala Cys Val Ile Gln Glu Val Trp Met Glu Gly Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165
```